(12) United States Patent
Semingson et al.

(10) Patent No.: US 10,085,778 B2
(45) Date of Patent: Oct. 2, 2018

(54) ROD REDUCER INSTRUMENT FOR SPINAL SURGERY

(71) Applicant: Spinal Elements, Inc., Carlsbad, CA (US)

(72) Inventors: Taylor Semingson, San Diego, CA (US); Eugene Shoshtaev, Del Mar, CA (US); Greg Martin, Carlsbad, CA (US); Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 15/447,661

(22) Filed: Mar. 2, 2017

(65) Prior Publication Data

US 2017/0252074 A1 Sep. 7, 2017

Related U.S. Application Data

(60) Provisional application No. 62/303,593, filed on Mar. 4, 2016.

(51) Int. Cl.
*A61B 17/88* (2006.01)
*A61B 17/70* (2006.01)
*A61B 90/00* (2016.01)

(52) U.S. Cl.
CPC ...... *A61B 17/7086* (2013.01); *A61B 17/7091* (2013.01); *A61B 2090/0808* (2016.02); *A61B 2090/0811* (2016.02)

(58) Field of Classification Search
CPC ............ A61B 17/7086; A61B 17/7091; A61B 2090/0808; A61B 2090/0811
USPC ................. 606/279, 264, 99, 104, 105, 86 A
See application file for complete search history.

(56) References Cited

U.S. PATENT DOCUMENTS 2,102,602 A * 12/1937 Nash ....................... B25B 1/125
269/179
3,604,487 A 9/1971 Gilbert
(Continued)

FOREIGN PATENT DOCUMENTS

DE 42 38 339 5/1994
EP 2 098 178 12/2011
(Continued)

OTHER PUBLICATIONS

U.S. Appl. No. 60/422,455, filed Oct. 30, 2003, Landry et al.
(Continued)

*Primary Examiner* — Pedro Philogene
*Assistant Examiner* — David C Comstock
(74) *Attorney, Agent, or Firm* — Knobbe, Martens, Olson & Bear, LLP

(57) ABSTRACT

Embodiments of a rod reducer and methods of using a rod reducer are provided. In some embodiments, the rod reducer includes a sleeve comprising a lumen and one or more tabs; an engagement member comprising a distal portion and a proximal portion, wherein the proximal portion is configured to be rotated relative to the distal portion; and a collar coupled to the sleeve, wherein the collar is configured to deflect the tabs inward into the lumen. In some embodiments, the rod reducer has a first configuration wherein the tabs engage the proximal portion and the proximal portion can be rotated to translate the engagement member and the rod reducer has a second configuration wherein the proximal portion can be pushed or pulled to translate the engagement member.

24 Claims, 21 Drawing Sheets

(56) References Cited

U.S. PATENT DOCUMENTS

| | | |
|---|---|---|
| 4,411,259 A | 10/1983 | Drummond |
| 5,020,519 A | 6/1991 | Hayes et al. |
| 5,364,397 A | 11/1994 | Hayes et al. |
| 5,449,361 A | 9/1995 | Preissman |
| 5,720,751 A | 2/1998 | Jackson |
| 5,782,830 A | 7/1998 | Farris |
| 5,810,378 A | 9/1998 | Brinkley |
| 5,810,878 A | 9/1998 | Burel et al. |
| 5,910,141 A | 6/1999 | Morrison et al. |
| 6,036,692 A | 3/2000 | Burel et al. |
| 6,342,057 B1 | 1/2002 | Brace et al. |
| 6,440,133 B1 | 8/2002 | Beale et al. |
| 6,530,929 B1 | 3/2003 | Justis et al. |
| 6,660,006 B2 | 12/2003 | Markworth et al. |
| 6,660,022 B1 | 12/2003 | Li et al. |
| 6,736,829 B1 | 5/2004 | Li et al. |
| 6,790,209 B2 | 9/2004 | Beale |
| 6,830,574 B2 | 12/2004 | Heckele et al. |
| 6,916,323 B2 | 7/2005 | Kitchens |
| 7,008,422 B2 | 3/2006 | Foley et al. |
| 7,011,660 B2 | 3/2006 | Sherman et al. |
| 7,041,120 B2 | 5/2006 | Li et al. |
| 7,083,612 B2 | 8/2006 | Littrup et al. |
| 7,160,300 B2 | 1/2007 | Jackson |
| 7,179,261 B2 * | 2/2007 | Sicvol ............... A61B 17/7032 606/86 A |
| 7,188,626 B2 | 3/2007 | Foley et al. |
| 7,250,052 B2 | 7/2007 | Landry et al. |
| 7,306,603 B2 | 12/2007 | Boehm, Jr. et al. |
| 7,322,979 B2 | 1/2008 | Crandall et al. |
| 7,431,731 B2 | 10/2008 | Kitchens |
| 7,473,267 B2 | 1/2009 | Nguyen et al. |
| 7,476,240 B2 | 1/2009 | Raymond et al. |
| 7,491,218 B2 | 2/2009 | Landry et al. |
| 7,520,879 B2 | 4/2009 | Justis et al. |
| 7,527,638 B2 | 5/2009 | Anderson et al. |
| 7,563,264 B2 | 7/2009 | Landry et al. |
| 7,572,276 B2 | 8/2009 | Lim et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,618,442 B2 | 11/2009 | Spitler et al. |
| 7,648,506 B2 | 1/2010 | McCord et al. |
| 7,648,507 B2 | 1/2010 | Techiera et al. |
| 7,650,919 B2 | 1/2010 | Rhyne et al. |
| 7,666,189 B2 * | 2/2010 | Gerber ............... A61B 17/7074 606/104 |
| 7,686,809 B2 | 3/2010 | Triplett et al. |
| 7,691,132 B2 | 4/2010 | Landry et al. |
| 7,695,475 B2 | 4/2010 | Justis et al. |
| 7,717,944 B2 | 5/2010 | Foley et al. |
| 7,749,232 B2 | 7/2010 | Salerni |
| 7,758,617 B2 | 7/2010 | Iott et al. |
| 7,763,030 B2 | 7/2010 | Blau et al. |
| 7,763,055 B2 | 7/2010 | Foley |
| 7,776,040 B2 | 8/2010 | Markworth et al. |
| 7,794,479 B2 | 9/2010 | Aferzon |
| 7,824,410 B2 | 11/2010 | Simonson et al. |
| 7,862,595 B2 | 1/2011 | Foley et al. |
| 7,871,413 B2 | 1/2011 | Park et al. |
| 7,871,424 B2 | 1/2011 | Abdelgany |
| 7,875,031 B2 | 1/2011 | Chin et al. |
| 7,905,907 B2 | 3/2011 | Spitler et al. |
| 7,909,830 B2 | 3/2011 | Frigg et al. |
| 7,914,558 B2 | 3/2011 | Landry et al. |
| 7,918,878 B2 | 4/2011 | Songer et al. |
| 7,922,727 B2 | 4/2011 | Songer et al. |
| 7,922,731 B2 | 4/2011 | Schumacher et al. |
| 7,951,152 B2 | 5/2011 | Marino |
| 7,967,826 B2 | 6/2011 | Colleran et al. |
| 7,976,546 B2 | 7/2011 | Geist et al. |
| 7,998,144 B2 | 8/2011 | Schumacher et al. |
| 8,002,798 B2 | 8/2011 | Chin et al. |
| 8,034,084 B2 | 10/2011 | Landry et al. |
| 8,043,343 B2 | 10/2011 | Miller et al. |
| 8,048,129 B2 | 11/2011 | Forton et al. |
| 8,070,751 B2 | 12/2011 | Justis et al. |
| 8,075,592 B2 | 12/2011 | Landry et al. |
| 8,097,027 B2 | 1/2012 | Lim et al. |
| 8,105,361 B2 | 1/2012 | Anderson et al. |
| 8,246,624 B2 | 8/2012 | Forton et al. |
| 8,308,728 B2 | 11/2012 | Lott et al. |
| 8,343,160 B2 | 1/2013 | Techiera et al. |
| 8,439,924 B1 * | 5/2013 | McBride ............ A61B 17/7085 606/104 |
| 8,603,094 B2 | 12/2013 | Walker et al. |
| RE44,813 E | 3/2014 | Beale et al. |
| 8,734,490 B2 | 5/2014 | Anderson et al. |
| 8,864,767 B2 | 10/2014 | Blain et al. |
| 9,833,268 B2 * | 12/2017 | Walker ............... A61B 17/7086 |
| 2003/0225408 A1 | 12/2003 | Nichols et al. |
| 2004/0172022 A1 | 9/2004 | Landry et al. |
| 2005/0090824 A1 | 4/2005 | Shluzas et al. |
| 2005/0192571 A1 | 9/2005 | Abdelgany |
| 2005/0192579 A1 | 9/2005 | Jackson et al. |
| 2005/0240275 A1 | 10/2005 | Chappuis |
| 2006/0079909 A1 | 4/2006 | Runco et al. |
| 2006/0142761 A1 | 6/2006 | Landry et al. |
| 2006/0200128 A1 | 9/2006 | Mueller |
| 2006/0229614 A1 | 10/2006 | Foley et al. |
| 2007/0005146 A1 | 1/2007 | Heyligers et al. |
| 2007/0016194 A1 | 1/2007 | Shaolian et al. |
| 2007/0173831 A1 | 7/2007 | Abdou |
| 2007/0270867 A1 | 11/2007 | Miller et al. |
| 2007/0270869 A1 | 11/2007 | Young et al. |
| 2008/0039839 A1 | 2/2008 | Songer et al. |
| 2008/0077138 A1 | 3/2008 | Cohen et al. |
| 2008/0077139 A1 | 3/2008 | Landry et al. |
| 2008/0161857 A1 | 7/2008 | Hestad et al. |
| 2008/0228228 A1 | 9/2008 | Hestad et al. |
| 2008/0243190 A1 * | 10/2008 | Dziedzic ............ A61B 17/7091 606/278 |
| 2008/0249531 A1 | 10/2008 | Patterson |
| 2008/0269805 A1 | 10/2008 | Dekutoski et al. |
| 2008/0312703 A1 | 12/2008 | Hestad et al. |
| 2009/0012563 A1 | 1/2009 | Alleyne et al. |
| 2009/0062857 A1 | 3/2009 | Ramsay et al. |
| 2009/0082809 A1 | 3/2009 | Nguyen et al. |
| 2009/0105774 A1 | 4/2009 | Jones et al. |
| 2009/0125032 A1 | 5/2009 | Gutierrez et al. |
| 2009/0143828 A1 | 6/2009 | Stad et al. |
| 2009/0171391 A1 | 7/2009 | Hutton et al. |
| 2009/0182382 A1 | 7/2009 | Justis et al. |
| 2009/0312797 A1 | 12/2009 | Lim et al. |
| 2009/0326586 A1 | 12/2009 | Duarte |
| 2010/0094359 A1 | 4/2010 | Techiera et al. |
| 2010/0222828 A1 | 9/2010 | Stad et al. |
| 2010/0228303 A1 | 9/2010 | Salerni |
| 2010/0249856 A1 | 9/2010 | Iott et al. |
| 2010/0331901 A1 | 12/2010 | Iott et al. |
| 2011/0022088 A1 | 1/2011 | Forton et al. |
| 2011/0071571 A1 | 3/2011 | Abdelgany |
| 2011/0152940 A1 | 6/2011 | Frigg et al. |
| 2011/0152942 A1 | 6/2011 | Oh et al. |
| 2011/0184464 A1 | 7/2011 | Fiorella |
| 2011/0196426 A1 | 8/2011 | Peukert et al. |
| 2011/0218581 A1 | 9/2011 | Justis |
| 2011/0238117 A1 | 9/2011 | Geist et al. |
| 2012/0283786 A1 * | 11/2012 | Rezach ............... A61B 17/7085 606/305 |
| 2014/0148865 A1 * | 5/2014 | Hennard ............ A61B 17/7086 606/86 A |
| 2015/0066042 A1 | 3/2015 | Cummins et al. |

FOREIGN PATENT DOCUMENTS

| | | |
|---|---|---|
| EP | 1 558 157 | 11/2012 |
| WO | WO 2005/023125 | 3/2005 |
| WO | WO 2016/077208 | 5/2016 |

OTHER PUBLICATIONS

U.S. Appl. No. 60/466,091, filed Apr. 28, 2003, Landry et al.

(56) References Cited

OTHER PUBLICATIONS

Foley et al., "Minimally Invasive Lumbar Fusion", Spine, 2003, vol. 28, No. 15S, pp. S26-S35.
Foley et al., "Percutaneous Pedicle Screw Fixation of the Lumbar Spine: Preliminary Clinical Results", Journal of Neurosurgery, Spine 1, 2002, vol. 97, pp. 7-12.
Khoo et al., "Minimally Invasive Percutaneous Posterior Lumbar Interbody Fusion", Neurosurgery, Nov. 2002, vol. 51, No. 2, pp. 166-181.
Kim et al., "Minimally Invasive Spine Instrumentation", Neurosurgery, Nov. 2002, vol. 51, No. 2, pp. 15-25.
McAfee et al., "Minimally Invasive Anterior Retroperitoneal Approach to the Lumbar Spine", SPINE, 1998, vol. 23, No. 13, pp. 1476-1484.
Newton et al., "Thoracoscopic Multilevel Anterior Instrumented Fusion in a Goat Model", SPINE, 2003, vol. 28, No. 14, pp. 1614-1620.
Onibokun et al., "Minimally Invasive Pedicle Screw Fixation", Operative Techniques in Neurosurgery, 2005, vol. 7, pp. 72-78.
Salerni, Anthony A., "Minimally Invasive Removal or Revision of Lumbar Spinal Fixation", The Spine Journal, 2004, vol. 4, No. 6, pp. 701-705.
Shamie et al., "Minimally Invasive Spinal Surgery", Operative Techniques in Orthopaedics, Jul. 2003, vol. 13, No. 3, pp. 202-206.
Teitelbaum et al., "New Percutaneously Inserted Spinal Fixation System", SPINE, Mar. 15, 2004, vol. 29, No. 6, pp. 703-709.
Wang et al., "Minimally Invasive Lateral Mass Screws in the Treatment of Cervical Facet Dislocations: Technical Note", Neurosurgery, Feb. 2003, vol. 52, No. 2, pp. 444-448.

\* cited by examiner

ROD REDUCER INSTRUMENT FOR SPINAL SURGERY

CROSS-REFERENCE TO RELATED APPLICATIONS

This application claims priority benefit to U.S. Provisional Patent Application No. 62/303,593, filed Mar. 4, 2016, which is hereby incorporated by reference herein in its entirety.

BACKGROUND

Field

The present disclosure relates to surgical instruments and in some arrangements to a surgical instrument for moving one part of a surgical implant into an adjacent position or contact with another.

Description of the Related Art

In orthopedic surgery, and particularly in spinal surgery, it is well known to correct an injury, malformation, or other defect using an implanted rod affixed to a body part to be corrected. For example, rod systems have been developed for correcting the positioning of and stabilizing of the spine, and for facilitating fusion at various levels of the spine. In one such system, the rod or elongated implant can be disposed longitudinally along a length of the spine. The rod can be bent, either prior to or during surgery, to correspond to the normal curvature of the spine in the particular region being instrumented, or to such other curvature as the surgeon may deem appropriate to correct the defect. For example, the rod can be bent to form a normal kyphotic curvature for the thoracic region of the spine, or to form a normal lordotic curvature for the lumbar region. The rod can then be attached or engaged to a number of fasteners which have been inserted or implanted into the vertebrae along the segment of the spinal column.

Fasteners are well known in the art and can include all types of bone screws, hooks, bolts, etc. configured to engage the vertebrae. For instance, one such fastener is a laminar hook, configured to engage a lamina of the vertebra. Another prevalent fastener is a spinal screw which can be threaded into a pedicle or other portion of vertebral bone. Examples of spinal screws include monoaxial spinal screws and polyaxial spinal screws.

In some spinal procedures, rods are coupled to two or more fasteners that are fixed to vertebrae, for instance at opposite sides of the spine or spinous processes. The fasteners can be threaded into a portion of several vertebral bodies, such as the pedicles of these vertebrae. The rod can be coupled to the bone screws to provide corrective and stabilizing forces to the spine. Affixing a rod to a fastener generally requires the rod to be in an adjacent position or in contact with the fastener. This may require that the rod and implanted fastener be moved with respect to each other so that the rod occupies space within a channel or other opening in the fastener. The rod can be coupled to the implanted fastener using a set screw, plug or other appropriate closure device. The process of placing a rod within or adjacent to an implanted fastener so that they can be coupled together is termed "reducing" the rod.

Rod reduction is commonly performed by a surgeon using his or her hands and/or rigid tools such as pliers, levers or other instruments able to create the necessary pushing and/or pulling forces on the implanted fastener and rod. Such procedures generally require the surgeon to place the rod directly over the implanted fastener, often intersecting a longitudinal axis of the fastener. Consequently, access to the rod and the fastener directly above the channel in the fastener into which the rod is to be placed can be necessary or at least highly desirable. However, such access can be difficult depending on such factors as the malformation to be corrected and the overall physiology of the patient. Additionally, during minimally invasive surgery, access can be very difficult as a result of the small ports or incisions of such procedures. With use of monoaxial fasteners, the physiology of the patient can require that the screw be placed at an angle such that the surgeon would have difficulty accessing and exerting force in the necessary orientation on the rod and/or the fastener. With polyaxial fasteners, the orientation of an rod-receiving part of the fastener can be varied with respect to the rod and/or the surgeon. Consequently, the surgeon is frequently faced with the task of reducing a rod from an awkward angle.

SUMMARY

In some embodiments, a rod reducer is provided. The rod reducer can include a sleeve comprising a lumen and one or more tabs. The rod reducer can include an engagement member comprising a distal portion and a proximal portion. In some embodiments, the proximal portion is configured to be rotated relative to the distal portion. The rod reducer can include a collar coupled to the sleeve. In some embodiments, the collar is configured to deflect the tabs inward into the lumen. In some embodiments, the rod reducer has a first configuration wherein the tabs engage the proximal portion and the proximal portion is configured to be rotated to translate the engagement member. In some embodiments, the rod reducer has a second configuration wherein the proximal portion can be pushed or pulled to translate the engagement member.

In some embodiments, the sleeve comprises a pair of legs separated by a slot. In some embodiments, the pair of legs is configured to remain straight in the first configuration and the second configuration. In some embodiments, the collar is configured to be rotated to switch between the first configuration and the second configuration. In some embodiments, the sleeve and the engagement member each comprise a marking, wherein alignment of the markings indicates a position to switch between the first configuration and the second configuration. In some embodiments, the sleeve and the engagement member each comprise a marking, wherein alignment of the markings indicates a distal position of the engagement member. In some embodiments, the sleeve and the engagement member each comprise a marking, wherein alignment of the markings indicate a maximum distal position of the engagement member for coupling the rod reducer to a fastener. In some embodiments, the tabs comprise threads and the proximal portion of the engagement member comprises threads. In some embodiments, the sleeve comprises one or more notches near a distal end, the one or more notches configured to allow the sleeve to rotate relative to a fastener. In some embodiments, the sleeve and the distal portion of the engagement member comprise a mating configuration. In some embodiments, the mating configuration comprises an undercut. In some embodiments, the rod reducer includes one or more alignment features configured to ensure alignment of the mating configuration. In some embodiments, in the mating configuration, the distal portion of the engagement member prevents a pair of legs of the sleeve from deflecting. In some embodiments, the engagement member comprises a lumen configured to accept a set screw.

In some embodiments, a method of using a rod reducer is provided. The method can include the step of pushing or pulling a proximal portion of an engagement member to translate a distal portion of the engagement member within a lumen of a sleeve. The method can include the step of rotating a collar to deflect one or more tabs into engagement with the proximal portion of the engagement member. The method can include the step of rotating the proximal portion of the engagement member to translate the distal portion of the engagement member within the lumen of the sleeve.

The method can include the step of engaging a thread of one or more tabs with a thread of the proximal portion of the engagement member. The method can include the step of rotating the proximal portion of the engagement member relative to the distal portion of the engagement member. The method can include the step of engaging an undercut of the sleeve with the distal portion of the engagement member. The method can include the step of coupling the distal portion of the sleeve to a fastener. The method can include the step of rotating the sleeve to decouple the distal portion of the sleeve from the fastener. The method can include the step of aligning a marking of the sleeve with a marking of the engagement member prior to rotating the collar. In some embodiments, aligning a marking of the sleeve with a marking of the engagement member indicates that a thread of the one or more tabs aligns with a thread of the proximal portion of the engagement member. In some embodiments, the proximal portion of the engagement member is rotated until a marking of the sleeve is aligned with a marking of the engagement member indicating that the distal portion of the engagement member is in a distalmost position. In some embodiments, aligning a marking of the sleeve with a marking of the engagement member indicates when the distal portion of the engagement member is sufficiently coupled with the sleeve to prevent a pair of legs of the sleeve from unintentionally disengaging from a fastener.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The structure and method of using the rod reducer will be better understood with the following detailed description of embodiments, along with the accompanying illustrations, in which.

DETAILED DESCRIPTION

Figure 1:
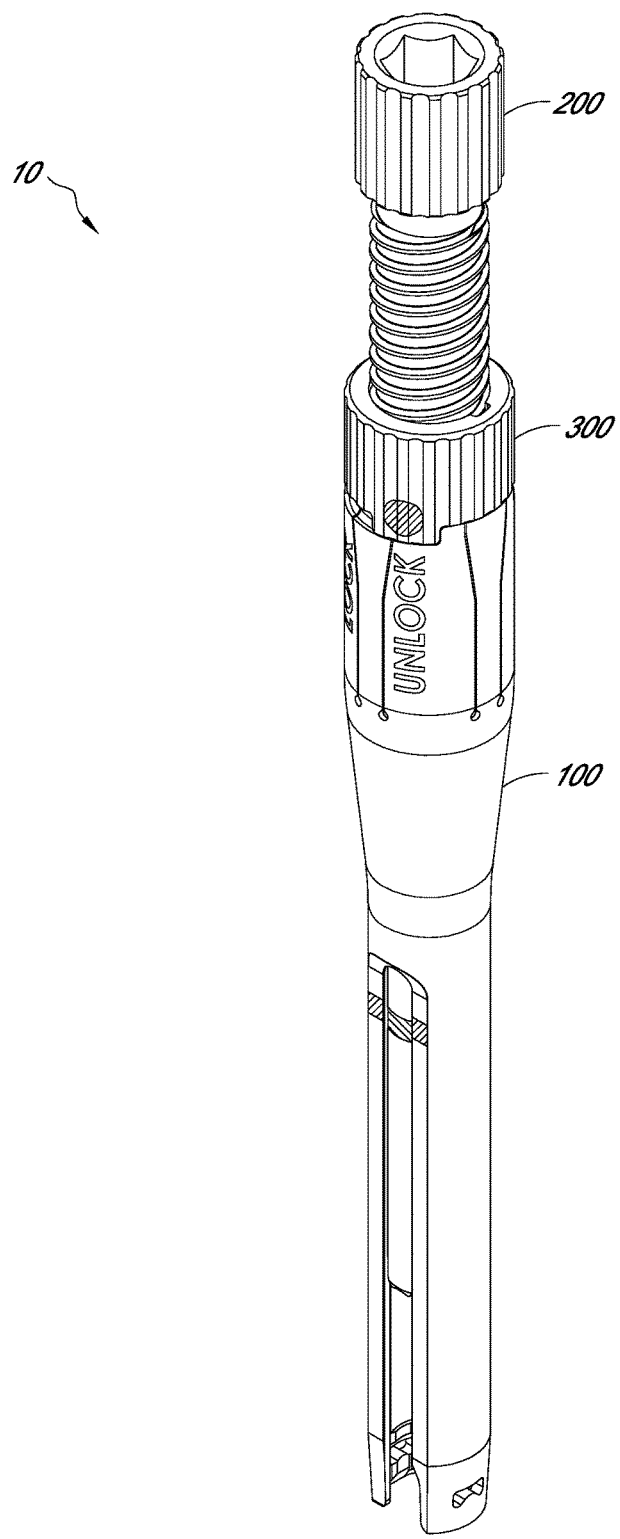
FIG. 1 illustrates a perspective view of a rod reducer according to an embodiment.

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Orthopedic devices such as rods can be secured to a bone using fasteners. The reduction of the rod within a channel of fastener may be directed by a rod reducer for more precise placement, especially for surgical sites with limited access or visibility, such as the cervical spine. The success or failure of the rod can often depend upon the precise placement of the rod within the channel of fastener. The rods utilized for spinal surgery can often be bent away from the fastener. The preferred trajectory of the rod may be perpendicular to the channel of the fastener such that the rod can be seated within the channel of the fastener. The rod may need to be lowered or reduced relative to the channel of the fastener. In some embodiments, a rod reducer is provided that facilitates proper placement of the rod relative to the fastener. The rod reducer can have the additional functionality of reliably and rapidly releasing the rod reducer after rod reduction.

Although referred to as rod reducer instruments, these instruments need not be used with only rods but can be used for the movement of any two objects toward each other for any of a number of purposes. For example, the rod reducer instruments can also facilitate delivery of components within interbody implants.

A. Anatomy of the Spine

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-15), five fused sacral (S1-S5) and four fused coccygeal vertebrae. Each vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae.

The typical cervical vertebrae differ from the other vertebrae with relatively larger spinal canals, oval shaped vertebral bodies, bifid spinous processes and foramina in their transverse processes. These foramina transversaria contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

The typical lumbar vertebrae are distinguishable from the other vertebrae by the absence of foramina transversaria and the absence of facets on the surface of the vertebral body. The lumbar vertebral bodies are larger than the thoracic vertebral bodies and have thicker pedicles and laminae projecting posteriorly. The vertebral foramen is triangular in shape and larger than the foramina in the thoracic spine but smaller than the foramina in the cervical spine. The superior and inferior articular processes project superiorly and inferiorly from the pedicles, respectively.

The rods described herein can be located at any level of the vertebral column. The rods can be positioned between adjacent vertebra in the vertebral column. In the description herein, the rod is described as positioned between a superior vertebra and an inferior vertebra. It should be appreciated that the rod can be utilized in other portions of the spine other than between adjacent vertebra.

The desired orientation of the rod can depend on the adjacent vertebra. The rod can be placed at any angle to the transverse plane, including parallel, substantially parallel, perpendicular, substantially perpendicular, 0 degrees, 15 degrees, 30 degrees, 45 degrees, 60 degrees, 75 degrees, 90 degrees, etc. The rod can be placed at any angle to the frontal plane, including parallel, substantially parallel, perpendicular, substantially perpendicular, 0 degrees, 15 degrees, 30 degrees, 45 degrees, 60 degrees, 75 degrees, 90 degrees, etc. The rod reducer instrument can facilitate placement of the rod relative to the fasteners while maintaining the desired orientation of the rod.

B. Rod Reducer Instruments

FIG. 1 depicts a perspective view of an embodiment of a rod reducer 10. As shown in FIG. 1, the rod reducer 10 can comprise a sleeve 100. The sleeve 100 can facilitate placement of the rod reducer 10 relative to a fastener (not shown). The rod reducer 10 can comprise an engagement member 200. The engagement member 200 can facilitate movement of the rod (not shown) relative to the fastener. The rod reducer 10 can comprise a collar 300. The collar 300 can allow for rapid release of the engagement member 200 relative to the sleeve 100. Further functionality of the rod reducer 10 is described in greater detail herein.

The rod reducer 10 can be used to engage the fastener and the rod to reduce the rod, or force the rod into engagement with the fastener such as a channel of a fastener. The sleeve 100 can be used to engage and secure the rod reducer 10 to a fastener, such as a bone screw. In some embodiments, the collar 300 is rotated to a disengaged position. This disengages a threaded portion of the sleeve 100 with a threaded portion of the engagement member 200. The engagement member 200 can be pushed in a longitudinal direction. The engagement member 200 can be moved distally until a first marking on the engagement member 200 aligns with a marking on the sleeve 100.

In some embodiments, the collar 300 is rotated to an engagement position. This engages the threaded portion of the sleeve 100 with the threaded portion of the engagement member 200. The engagement member 200 can be rotated which causes longitudinal translation of the engagement member 200 within the sleeve 100. The engagement member 200 slides within a lumen of the sleeve 100 and makes contact with the rod. Further movement of the engagement member 200 causes the rod to be drawn toward the fastener to seat the rod within a channel of the fastener. The engagement member 200 can be moved distally until a second marking on the engagement member 200 aligns with a marking on the sleeve 100. The second marking can indicate that the rod has been fully reduced relative to the fastener.

Additional instruments can be inserted within the engagement member 200 to secure the rod to the fastener. In some embodiments, a closure device such as a set screw is inserted within a lumen of the engagement member 200 toward the fastener. The closure device can maintain the position of the rod within the channel of the fastener.

Once the rod is secured, the rod reducer 10 can be released from the fastener. The engagement member 200 can be rotated which causes longitudinal translation of the engagement member 200 within the sleeve 100. The engagement member 200 slides within a lumen of the sleeve 100. In some embodiments, the collar 300 is rotated to a disengaged position. This disengages the threaded portion of the sleeve 100 with the threaded portion of the engagement member 200. The engagement member 200 can be pulled in a longitudinal direction. In some embodiments, the engagement member 200 is removed from the sleeve 100 prior to disengaging the fastener. In other embodiments, the engagement member 200 is removed from the sleeve 100 after disengaging the fastener. The sleeve 100 can be rotated to disengage the rod reducer 10 from the fastener. The components that perform these functions are described in greater detail herein.

1. Sleeve

Figure 2:
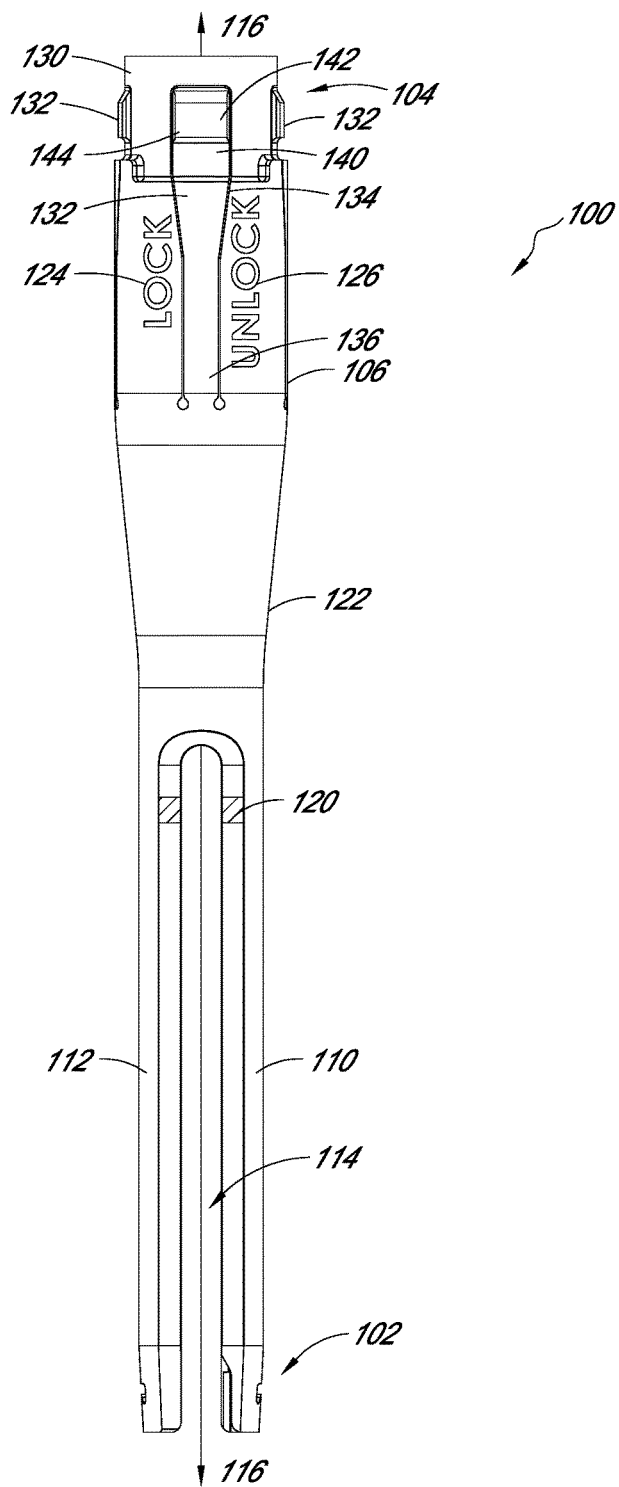
FIG. 2 is a front view of the sleeve of FIG. 1.

FIG. 2 is a front view of the sleeve 100 of FIG. 1. The sleeve 100 includes a distal end 102 and a proximal end 104. The distal end 102 can engage a fastener as described herein. The proximal end 104 can engage the collar 300 as described herein. The sleeve can include a grip 106 which facilitates the grip of the sleeve 100 during rod reduction. The grip 106 can include a plurality of longitudinal grooves. Other configurations are contemplated including raised protrusion, textured surfaces, etc.

The distal portion of the sleeve 100 includes a plurality of legs. In the illustrated embodiment, the distal portion can include two legs, 110, 112. The legs 110, 112 can be disposed 180 degrees relative to each other. Disposed between the legs 110, 112 can be a slot 114 which separates the legs 110, 112. The slot 114 can allow the distal end 102 to flex around a fastener as described herein. Each leg 110, 112 can be generally straight. Each leg 110, 112 can be parallel or substantially parallel to a longitudinal axis 116 of the sleeve 100. Each leg 110, 112 can have a neutral position in which the leg 110, 112 is equidistant from the longitudinal axis 116 from the proximal end of each leg 110, 112, to a distal end of each leg 110, 112.

The external surface shape of the legs 110, 112 can be generally circular or circular, as shown in FIG. 2. Other external shapes are contemplated including rectangular, polygonal, elliptical, etc. The external shape of the legs 110, 112 can mitigate trauma to the surrounding tissue during rod reduction. The external shape of the legs 110, 112 can correspond with the internal shape of a cannula utilized to insert the fastener and/or the rod reducer 10.

The sleeve 100 can include a marking 120. The marking can be a line, shape, icon, letter, number, word or other indicia. FIG. 2 shows a line as the marking 120. The marking 120 can include a plurality of markings, for instance diametrically opposed markings. Such diametrically opposed markings may allow the surgeon to view the markings 120 regardless of the orientation of the sleeve 100. The marking 120 can extend in a horizontal direction. The marking 120 can extend along a portion of a leg 110, 112. The marking 120 can extend along a portion of both legs 110, 112 as shown in FIG. 2.

The sleeve 100 can include a taper 122 that extends between the legs 110, 112 and the grip 106. The taper 122 can increase the cross-section of a proximal portion of the sleeve 100. The increased cross-section can help facilitate gripping of the rod reducer 10 during reduction.

The sleeve 100 can include a marking 124. The marking 124 can include a line, shape, icon, letter, number, or other indicia. The marking 124 can indicate the rotational position for an engaged position of the collar 300. The sleeve 10 can include a marking 126. The marking 126 can include a line, shape, icon, letter, number, or other indicia. The marking 126 can indicate the rotational position for an disengaged position of the collar 300. The marking 124, 126 can include a plurality of markings, for instance diametrically opposed markings. Such diametrically opposed markings may allow the surgeon to view the markings 124, 126 regardless of the orientation of the sleeve 100.

FIG. 2 shows words to indicate each rotational position. The marking 124 is labeled as "LOCK" and the marking 126 is labeled as "UNLOCK." Each marking 124, 126 is at a different rotational position along the sleeve 100. In some embodiments, the markings 124, 126 are separated by 45 degrees. Other rotational positions are contemplated for the markings 124, 126 including separated by 30 degrees, 60 degrees, 75 degrees, 90 degrees, etc. The position of the markings 124, 126 corresponds to the position of the collar 300 in the engaged position and disengaged position, respectively.

The sleeve 100 can include a cut out portion 130. The cut out portion 130 can be located proximal to the markings 124, 126. The cut out portion 130 can be shaped to accept the collar 300 as described herein. The collar 300 can be rotated to align with the markings 124, 126 as described herein. The cut out portion 130 limits the rotational freedom of the collar 300 relative to the sleeve 100. The cut out portion 130 can have a smaller diameter or width than the grip 106. The cut out portion 130 can have a diameter or width such that the collar 300, when placed within the cut out portion 130, and the grip 106 have the same or similar diameter or width.

The sleeve 100 can include one or more tabs 132. In the illustrated embodiment, the sleeve 100 includes four tabs 132. Other configurations are contemplated, e.g., one tabs, two tabs, three tabs, five tabs, six tabs, seven tabs, eight tabs, nine tabs, ten tabs, etc. Each tab 132 can comprise a cut 134 along three sides of a generally rectangular shape to form a perimeter of the tab. The cut 134 can begin in the grip 106 and extend to the cut out portion 130. In the illustrated embodiment, the cut 134 does not form a closed shape and the distal end of the tab 132 remains attached to the grip 106. As illustrated in FIG. 2, the distal end of the cut 134 can have round reliefs to help prevent the cut 134 from extending and to help the tab 132 flex at the distal hinge. The cut 134 allows the tab 132 to flex inward and outward as described herein.

Each tab 132 can have a distal portion 136. The distal portion 136 can have the same or similar external shape as the grip 106. The distal portion 136 can include a taper. The taper can increase the width of the tab from the distal portion 136 to a middle portion 140. The middle portion 140 of the tab 132 can have the same or similar external shape as the cut out portion 130. Each tab 132 can have a proximal portion 142. The proximal portion 142 can include a first engagement feature 144. In FIG. 2, the first engagement feature 144 is a protrusion. The first engagement feature 144 can engage a portion of the collar 300 to move the tab 132 inward. The neutral position of the tab 132 can be outward as shown in FIG. 2. The collar 300 can engage the first engagement feature 144 and move the tab 132 inward as described herein. The collar 300 can disengage the first engagement feature 144 thereby allowing the tab 132 to regain the neutral position of the tab 132.

Figure 3:
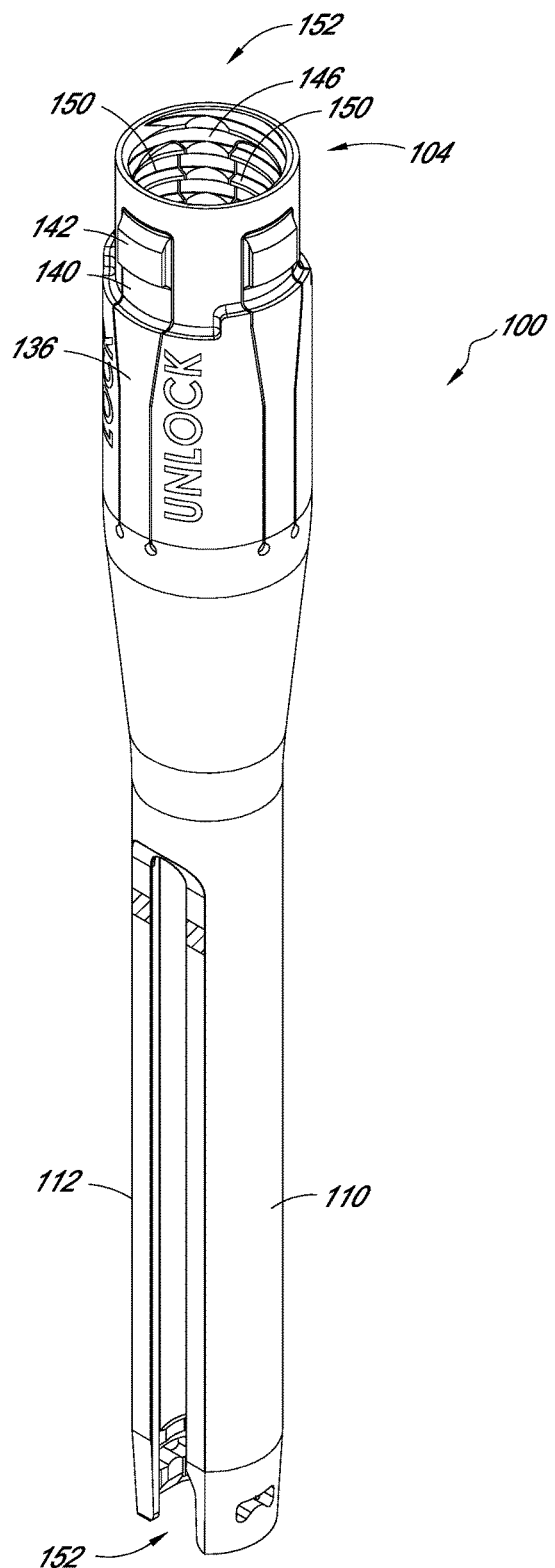
FIG. 3 is a perspective view of the proximal end of the sleeve of FIG. 2.

FIG. 3 is a perspective view of the proximal end 104 of the sleeve 100. The internal surface of the sleeve 100 can include threads 146. The threads 146 can extend from the proximal end 104 of the sleeve 100. The threads 146 can extend along the length of the cut out portion 130. The threads 146 can be formed during manufacturing. In some embodiments, the threads 146 do not threadingly engage with another component of the rod reducer 10 when the tabs 132 are in the neutral position.

Each tab 132 can include threads 150. The threads 146, 150 can be correspondingly timed to form continuous threads. The threads 150 on each tab 132 are correspondingly timed to form continuous threads. The threads 150 can extend from a distal end of the tab 132 along the length of the tab 132. In some embodiments, the threads 150 extend along at least part of the length of the proximal portion 142, the middle portion 140 and/or the distal portion 136 of the tab 132. In some embodiments, the threads 150 are disposed on only part of the length of the tab 132, such as on portions of only the proximal portion 142 and middle portion 140.

Figure 4:
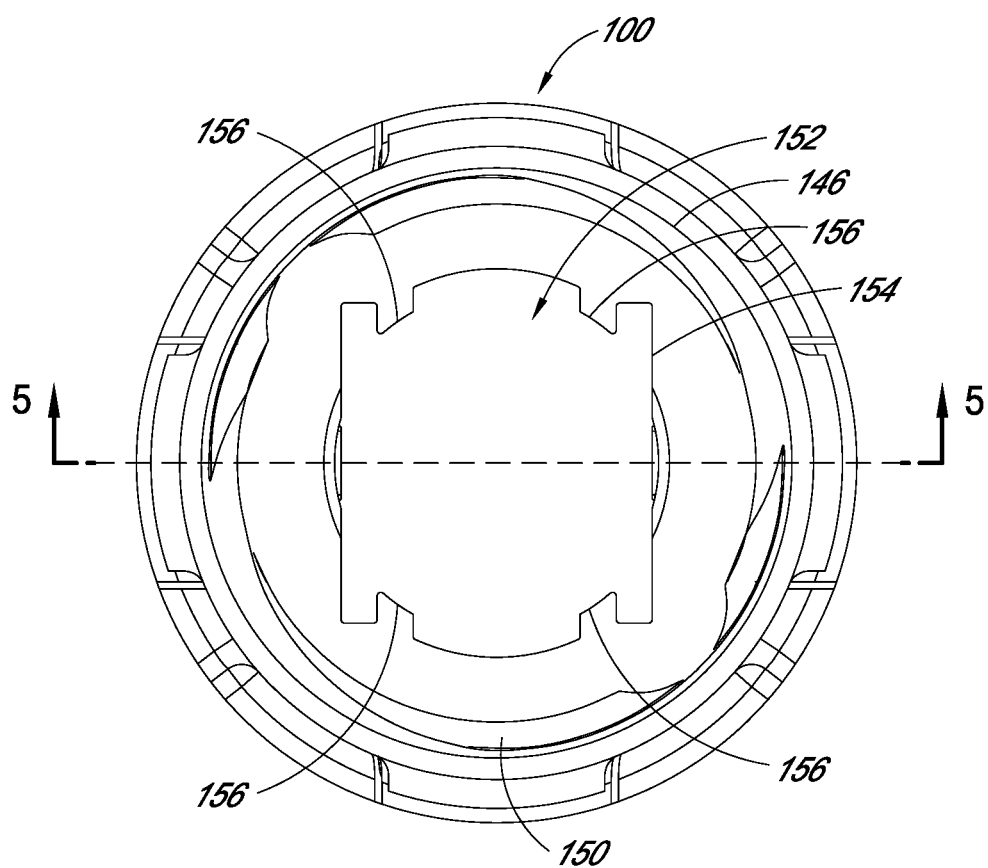
FIG. 4 is a top view of the sleeve of FIG. 2.
Figure 5:
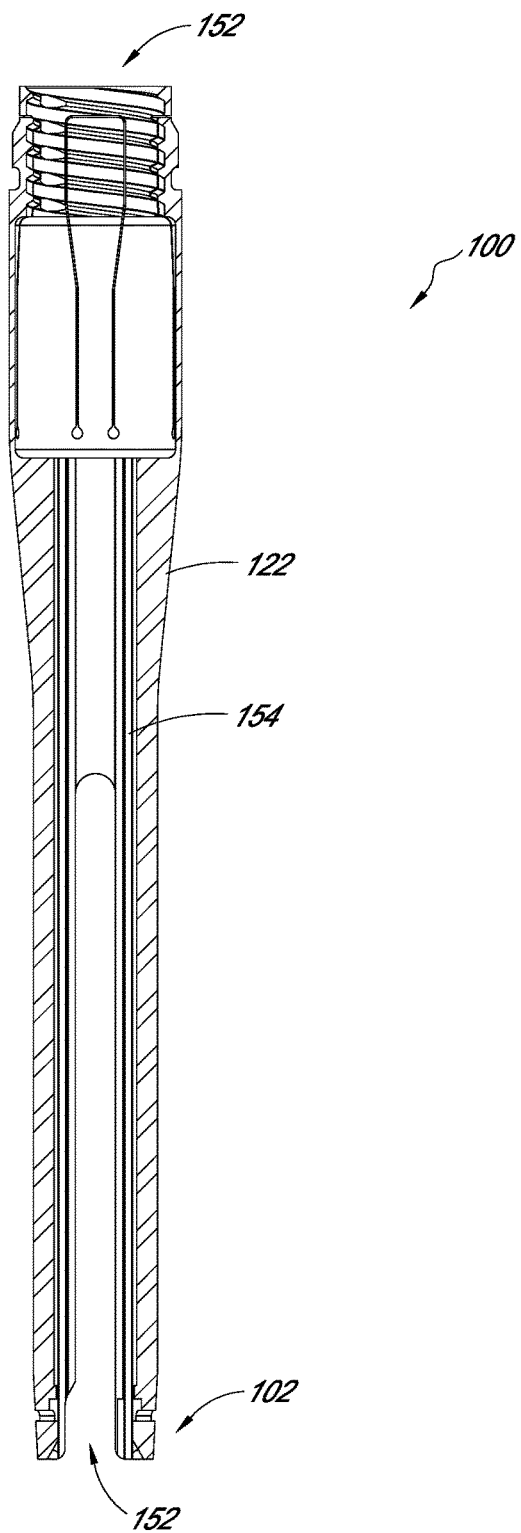
FIG. 5 is a cross-sectional view of the sleeve of FIG. 2 along lines 5-5 in FIG. 4.

The sleeve 100 can include a lumen 152 extending from the distal end 102 to the proximal end 104. The lumen 152 allows the engagement member 200 to be at least partially inserted within the sleeve 100 as described herein. The lumen 152 can have various shapes along the length of the sleeve. For instance, near the proximal end 104, the lumen 152 is formed from the threads 146, 150. For instance, near the distal end 102, the lumen 152 is formed from the legs 110, 112. FIG. 4 is a top view of the sleeve 100 of FIG. 2. FIG. 5 is a cross-sectional view of the sleeve 100 along lines 5-5 in FIG. 4. The lumen 152 can include a mating portion 154 having mating geometry. The mating geometry can be any cross-sectional shape that ensures a mating configuration between the sleeve 100 and the engagement member 200. In the illustrated embodiment, the mating portion 154 of the lumen 152 has a x-ring cross sectional shaped. The x-ring is formed of a generally circular cross-sectional shape having two intersecting longitudinal bars. The mating portion 154 can include undercuts 156 which guide the engagement member 200 relative to the sleeve 100. The mating portion 154 can extend from the distal end 102 as shown in FIG. 5. The mating portion 154 can extend to through the taper 122 as shown in FIG. 5. The mating portion 154 can extend any length along the lumen 152.

Figure 6:
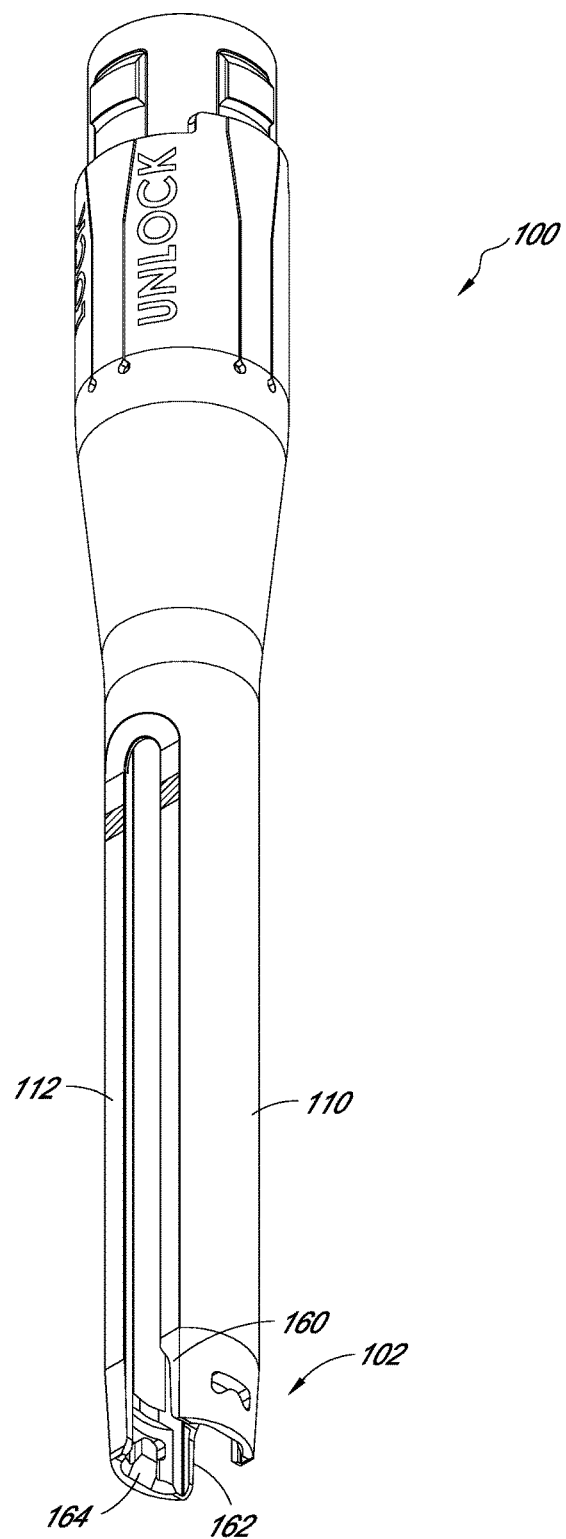
FIG. 6 is a perspective view of the distal end of the sleeve of FIG. 2.

FIG. 6 is a perspective view of the distal end 102 of the sleeve 100. The distal end 102 is configured to couple with the fastener (not shown). The distal end 102 can be shaped to accept a head of a polyaxial screw as described herein. The distal end 102 can be designed to mate with any known fastener, for instance, by including specific undercuts and shapes that can engage external features of the fastener.

The distal end 102 can include a pair of notches 160, 162. The notch 160 can be located on the leg 110, and the notch 162 can be located on the leg 112. The notches 160, 162 can be diametrically opposed. The notches 160, 162 can be designed to provide clearance around the head of the fastener when the sleeve 100 is rotated to disengage the sleeve 100 from the fastener. The notches 160, 162 can accommodate a leading edge of the head of the fastener as described herein.

Each leg 110, 112 can include one or more first couplers 164 to engage the head of the fastener. In the illustrated embodiment, the first couplers 164 are tabs which engage corresponding recesses in the head of the fastener. The sleeve 100 can be configured to accept the fastener in one of two orientations. For instance, each first coupler 164 can accept either one of two sides of the fastener. In other configurations, the sleeve 100 is configured to accept the fastener in only one orientation. For instance, each first coupler 164 can be unique such that each leg 110, 112 only mates with one particular side of the fastener. Other configurations for the distal end 102 of the sleeve 100 are contemplated based on the configuration of the fastener.

2. Engagement Member

Figure 7:
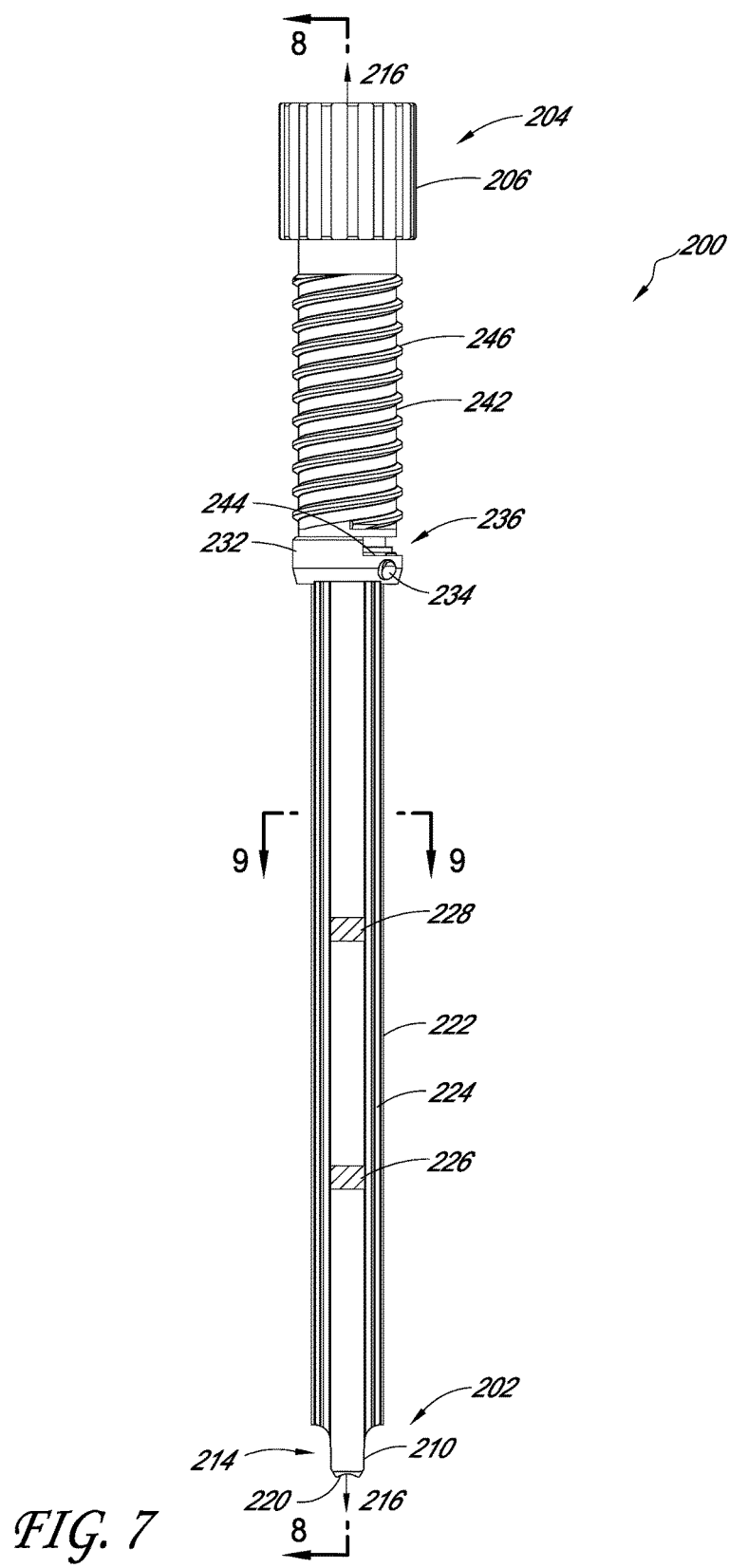
FIG. 7 is a front view of the engagement member of FIG. 1.
Figure 8:
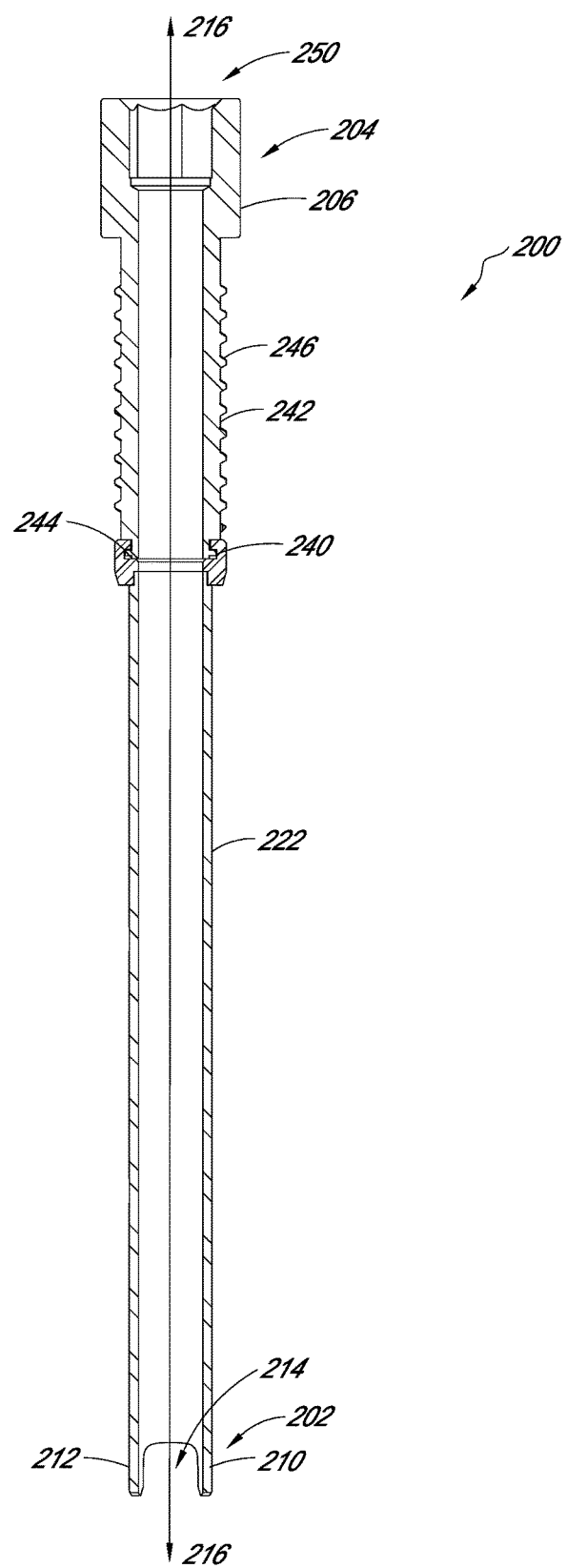
FIG. 8 is a cross-sectional view of the engagement member of FIG. 7 along lines 8-8 in FIG. 7.

FIG. 7 is a front view of the engagement member 200 of FIG. 1. FIG. 8 is a cross-section view of FIG. 7. The engagement member 200 includes a distal end 202 and a proximal end 204. The distal end 202 can engage the rod as described herein. The proximal end 204 can include a handle 206. The handle 206 facilitates the grip of the engagement member 200 during rod reduction. The handle 206 can include a plurality of longitudinal grooves. Other configurations are contemplated including raised protrusion, textured surfaces, etc.

The engagement member 200 can include a first marking 226. The marking can be a line, shape, icon, letter, number, word or other indicia. FIG. 7 shows a line as the marking 226. The marking 226 can include a plurality of markings, for instance diametrically opposed markings. Such diametrically opposed markings may allow the surgeon to view the markings 226 regardless of the orientation of the engagement member 200 within the sleeve 100. The marking 226 can extend in a horizontal direction. The marking 226 can extend at a specific location along the longitudinal axis 216 of the engagement member 200.

The engagement member 200 can include a second marking 228. The marking can be a line, shape, icon, letter, number, word or other indicia. FIG. 7 shows a line as the second marking 228. The second marking 228 can include a plurality of markings, for instance diametrically opposed markings. Such diametrically opposed markings may allow the surgeon to view the second markings 228 regardless of the orientation of the engagement member 200 within the sleeve 100. The second marking 228 can extend in a horizontal direction. The second marking 228 can be more proximal than the first marking 226. The second marking 228 can extend at a specific location along the longitudinal axis 216 of the engagement member 200. In some embodiments, the first marking 226 and the second marking 228 are the same indicia. In other embodiments, the first marking and the second marking are distinct indicia. For instance, the indicia can include different colors, shapes, thicknesses, etc. In some embodiments, the engagement member 200 has more than two markings, such as three or four markings at different vertical positions on the engagement member 200. For example, the engagement member 200 can have a third marking (not shown) between the first marking 226 and second marking 228. The third marking can be a line, shape, icon, letter, number, word or other indicia and can be similar to the first and second markings.

Referring to FIGS. 7 and 8, the distal portion of the engagement member 200 includes one or more of flanges to engage the rod. In the illustrated embodiment, the distal portion can include two flanges, 210, 212. The flanges 210, 212 can be disposed 180 degrees relative to each other. The flanges 210, 212 can include a slot 214 which separates the flanges 210, 212. Flanges 210, 212 can be relatively straight. Each flanges 210, 212 can be parallel or substantially parallel to a longitudinal axis 216 of the engagement member 200. Each flange 210, 212 can have a distal end 220 to engage the rod. The distal end 220 can be rounded to correspond to the rounded surface of a rod. Other shapes are contemplated.

The engagement member 200 can include a lumen 250 extending from the distal end 202 to the proximal end 204, as shown in FIG. 8. The lumen 250 allows other instrumentation to be at least partially inserted within the engagement member 200 as described herein. In some embodiments, a closure device can be inserted within the lumen 250 to couple the rod to the fastener. The lumen can be sized to accept a driver for the closure device.

Figure 9:
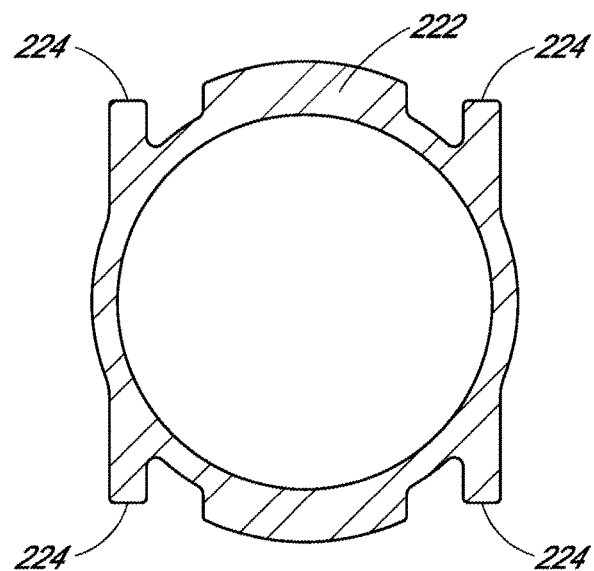
FIG. 9 is a cross-sectional view of the engagement member of FIG. 7 along lines 9-9 in FIG. 7.

The engagement member 200 can include a shaft 222. FIG. 9 is a cross-sectional view of the engagement member 200 of FIG. 7 along lines 9-9 in FIG. 7. The external surface of the shaft 222 can have a mating geometry. The engagement geometry can be any cross-sectional shape that ensures a mating configuration between the sleeve 100 and the engagement member 200. In the illustrated embodiment, the shaft 222 has a x-ring cross sectional shaped. The x-ring is formed of a generally circular cross-sectional shape having two intersecting longitudinal bars. The shaft 222 can include ridges 224 which interact with the undercuts 156 of the sleeve 100, shown in FIG. 4. The ridges 224 guide the engagement member 200 relative to the sleeve 100. The ridges 224 can extend above the slot 214. The ridges 224 can extend the length of the shaft 222. The ridge 224 can extend above the slot 214 and along a portion of the length of the shaft (e.g., half of the length of the shaft, a quarter of the length of the shaft, etc.). The ridges 224 can extend any length along the shaft 222.

Referring back to FIGS. 7 and 8, the engagement member 200 can include a junction 232. The junction 232 can be located at the proximal end of the shaft 222. In some embodiments, the junction 232 is integrally formed with the proximal end of the shaft 222. In other embodiments, the junction 232 is a separate component from the shaft 222. The junction 232 can include a first alignment feature 234. The first alignment feature 234 can be a pair of diametrically opposed pegs. The junction 232 can include a cut out portion 236. The junction 232 can include an undercut 240. The undercut 240 can allow portions of the engagement member 200 to rotate relative to each other.

The engagement member 200 can include a threaded member 242. The threaded member can include a ridge 244 as shown in FIG. 8. The ridge 244 can mate with the undercut 240 of the junction 232. The ridge 244 can allow the threaded member 242 to rotate relative to the junction 232. The ridge 244 prevents the threaded member from translating relative to the junction 232. The cut out portion 236 can allow the threaded member 242 to be disengaged from the junction 232. The cut out portion 236 can allow disassembly of the threaded member 242 for sterilization or for other purposes.

The threaded member 242 can include threads 246. The threads 246 can form a continuous helix. The threads 246 can begin at a location proximal to the ridge 244. The threads 246 can be correspondingly timed to engage the threads 150 of each tab 132, as described herein. The threads 246 can terminate near the handle 206.

3. Collar

Figure 10:
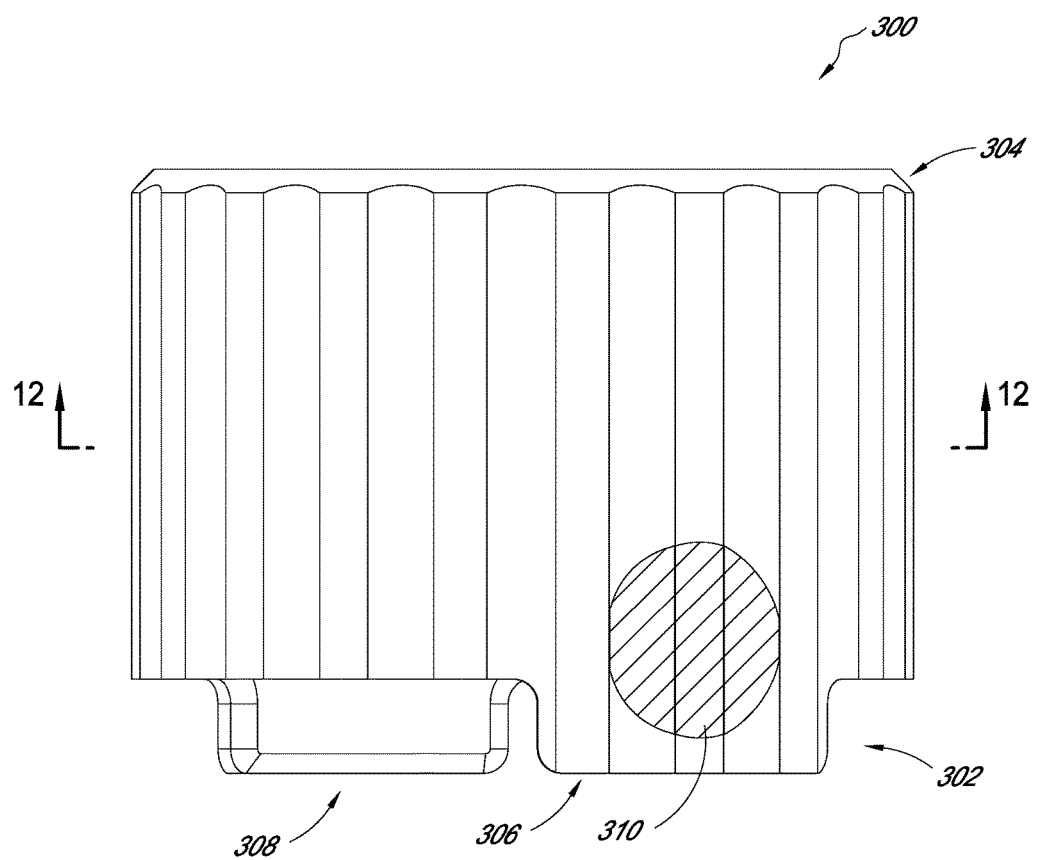
FIG. 10 is a front view of the collar of FIG. 1.

FIG. 10 is a front view of the collar 300 of FIG. 1. The collar 300 includes a distal end 302 and a proximal end 304. The collar 300 is shaped and sized to rotate relative to the cut out portion of 130 of the sleeve 100 as described herein. The collar 300 can include a cross sectional shape that is the same or similar to the sleeve 100.

The collar 300 can include one or more flanges. In the illustrated embodiment, the collar 300 includes two flanges 306, 308. Other configurations are contemplated. The flanges 306, 308 can be near the distal end 302 of the collar 300. The flange 306 can include a marking 310. The marking 310 can be a line, shape, icon, letter, number, or other indicia. FIG. 10 shows the marking 310 to be a dot. The marking 310 can include a plurality of markings, for instance diametrically opposed markings. Such diametrically opposed markings may allow the surgeon to view the markings 310 regardless of the orientation of the collar 300. The marking 310 can indicate the rotational position of the collar 300.

The collar 300 can be rotated relative to the sleeve 100 as described herein. The collar 300 can be rotated to align the marking 310 with marking 124 of the sleeve 100. This position can indicate that the collar 300 is in the engaged position. The collar 300 can be rotated to align the marking 310 with the marking 126 of the sleeve 100. This position can indicate that the collar 300 is in the disengaged position.

Figure 11:
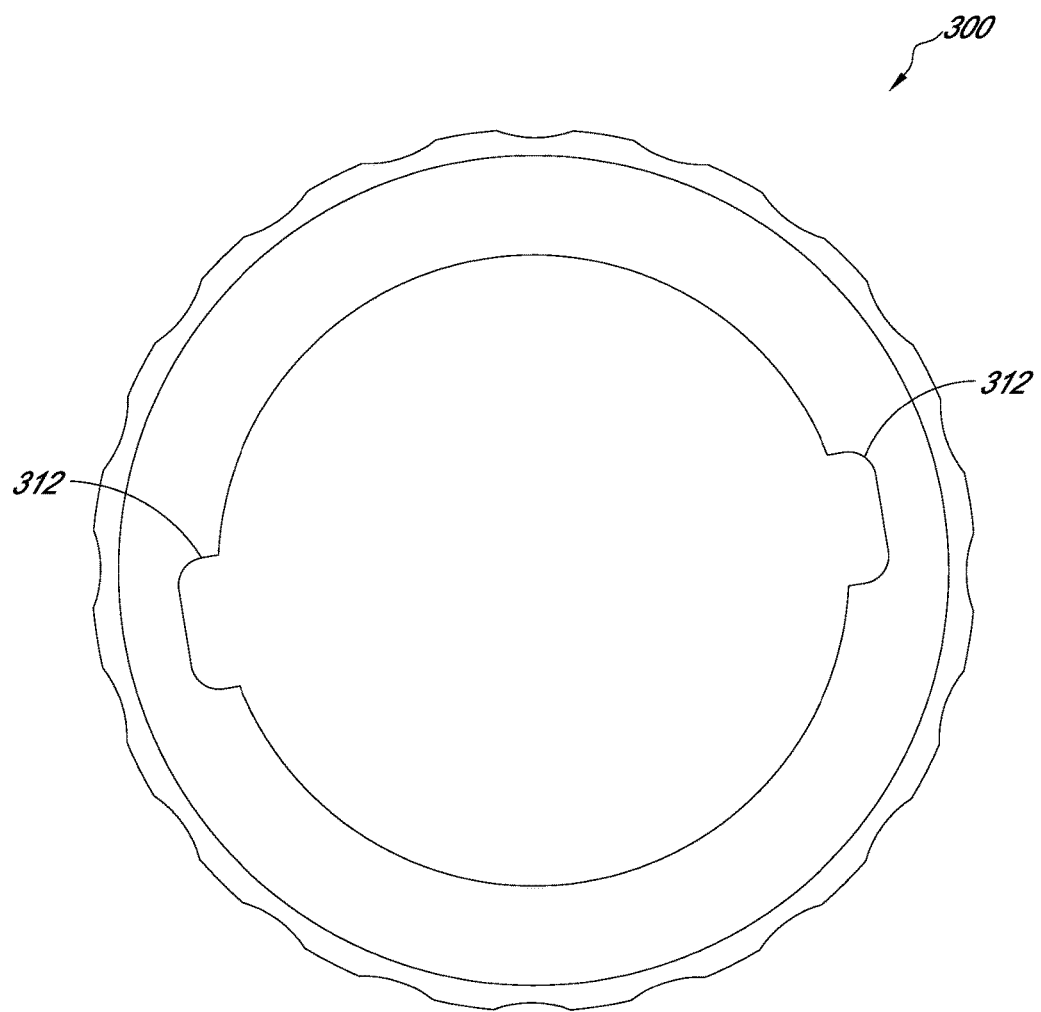
FIG. 11 is a top view of the collar of FIG. 10.

FIG. 11 is a top view of the collar 300. The collar 300 can include a second alignment feature 312. In FIG. 11, the second alignment feature 312 is a pair of diametrically opposed slots. The second alignment feature 312 of the collar 300 are sized to accept the first alignment feature 234 of the junction 232. In some embodiments, the opposed slots of the collar 300 are sized to accept the pegs of the junction 232. The collar 300 can be configured to accept the junction 232 in one of two orientations. For instance, each second alignment feature 312 can accept either first alignment feature 234. In other configurations, the collar 300 is configured to accept the junction 232 in only one orientation. For instance, each second alignment feature 312 can be unique such that each second alignment feature 312 of the collar 300 only accepts a particular first alignment feature 234 of the junction 232.

Figure 12:
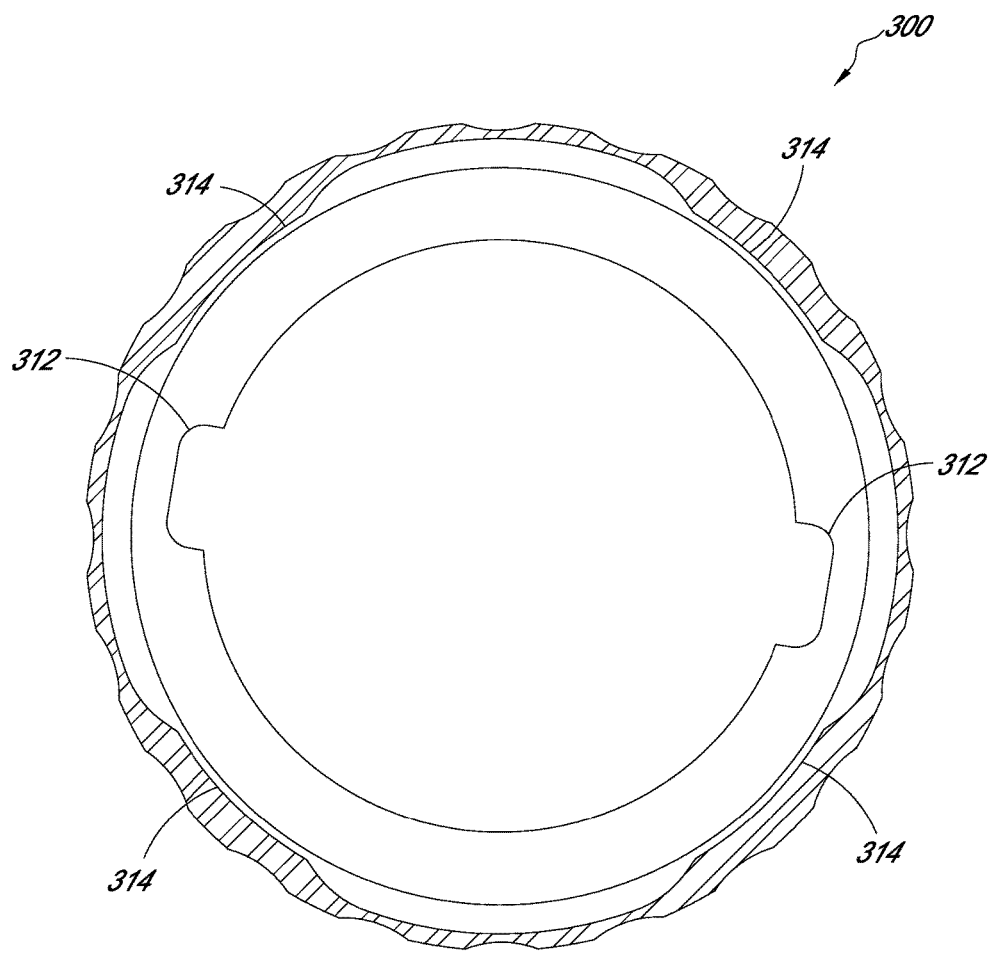
FIG. 12 is a cross-sectional view of the collar of FIG. 10 along lines 12-12.

FIG. 12 is a cross-sectional view of the collar 300 of FIG. 10 along lines 12-12. The collar 300 can include one or more second engagement features 314. In FIG. 10, the second engagement features 314 are a plurality of ramps. The second engagement features 314 interact with the first engagement features 144 of the tabs 132. In some embodiments, the ramps of the collar 300 interact with the protrusions of the tabs 132. In the engaged configuration of the collar 300, the second engagement features 314 push the tabs 132 inward. In the disengaged configuration of the collar 300, the second engagement features 314 do not push the tabs 132 inward. The tabs 132 can have a neutral position. In the disengaged configuration of the collar 300, the tabs 132 can regain the neutral position.

In other embodiments, the reducer 10 can have other functional engagement mechanisms to engage the sleeve 100 with the engagement member 200. For example, the reducer can include a clamp around the proximal end 104 of the sleeve 100. The clamp can have an inner diameter disposed around the tabs. When the clamp is actuated, the inner diameter can contract to engage the tabs and push the tabs inward, as described above. In another example, instead of a collar that is rotated to engage the tabs, the reducer can have a collar that is translated in the proximal-distal direction. The collar can have an inner diameter that decreases from the distal end to the proximal end. As the collar is translated distally, the decreasing inner diameter engages the tabs to push the tabs inward. Other functional engagement mechanisms are also contemplated.

4. Fastener and Rod

Figure 13:
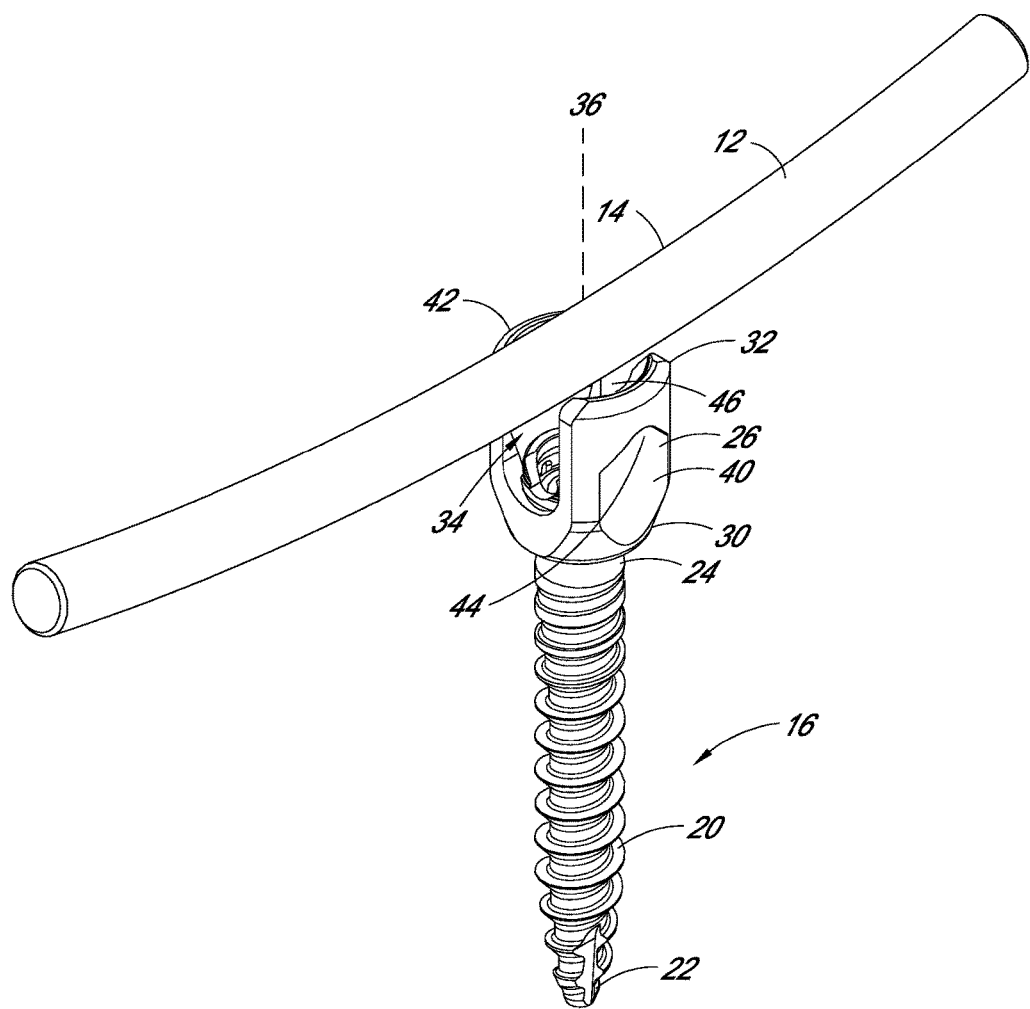
FIG. 13 is an embodiment of a rod and a fastener.

FIG. 13 is an embodiment of a rod 12. The rod 12 can include a bend 14. The bend 14 can correspond to a bend of the anatomy. The bend 14 can correspond to a desired outcome of the surgical procedure. The bend 14 can cause the rod 12 to extend proximally from a fastener 16.

The fastener 16 can be a polyaxial screw. The fastener 16 can include a screw 20. The screw 20 has a distal end 22 and a proximal end 24. During a method of use, the distal end 22 of the screw 20 can be driven into a vertebra. The fastener 16 can include a head 26. The head 26 can include a distal end 30 and a proximal end 32. The screw 20 and the head 26 can be coupled to allow polyaxial or uniaxial movement. The head 26 includes a channel 34. In FIG. 13, the channel 34 is U-shaped but other configurations are contemplated. The channel 34 is sized to accept the rod 12. The rod 12 can be inserted from the proximal end 32 of the head 26 toward the distal end 30 of the head 26. The head 26 can include a longitudinal axis 36.

The fastener 16 can include two sides 40, 42. Each side 40, 42 can include one or more second couplers 44. The second couplers 44 are configured to engage the first couplers 164 of the legs 110, 112 of the sleeve 100. In the illustrated embodiment, the second couplers 44 are recesses in the head 26 of the fastener 16. The head 26 of the fastener 16 can be accepted by the sleeve 100 in one of two orientations. For instance, each second coupler 44 can be accepted by either leg 110, 112. In other configurations, the sleeve 100 is configured to accept the head 26 in only one orientation. For instance, each second coupler 44 can be unique such that each leg 110, 112 only mates with one particular side 40, 42 of the fastener 16.

The proximal end 32 of the head 26 can include an opening 46. The opening 46 can be configured to accept a closure device (not shown). In some embodiments, the opening 46 is threaded to engage the corresponding threads of the closure device. The closure device can secure the rod 12 to the fastener 16, as described herein.

Other configurations of fasteners are contemplated. In some embodiments, the head 26 is integrally formed with the screw 20. In some embodiments, the fastener 16 includes a hook. The fastener 16 can include any structure having a corresponding channel 34 for the rod 12.

C. Method Steps of Use

FIGS. 13-21 illustrate various method steps which may be performed utilizing the rod reducer 10 described herein. In some embodiments, a method can comprise one or more of these steps. In some embodiments, a method can comprise any of the steps below in any order. In some embodiments, a method can include the same step at multiple times during the method of use.

FIG. 13 shows the head 26 coupled with the screw 20. The screw 20 can be driven into a vertebra. The rod 12 can be positioned adjacent to the fastener 16. The rod 12 can be aligned with the channel 34 of the head 26 of the fastener 16. As shown in FIG. 13, the rod 12 can be a distance from the distal end 30 of the head 26. This distance is decreased during rod reduction such that the rod 12 is seated within the head 26 of the fastener 16.

Figure 14:
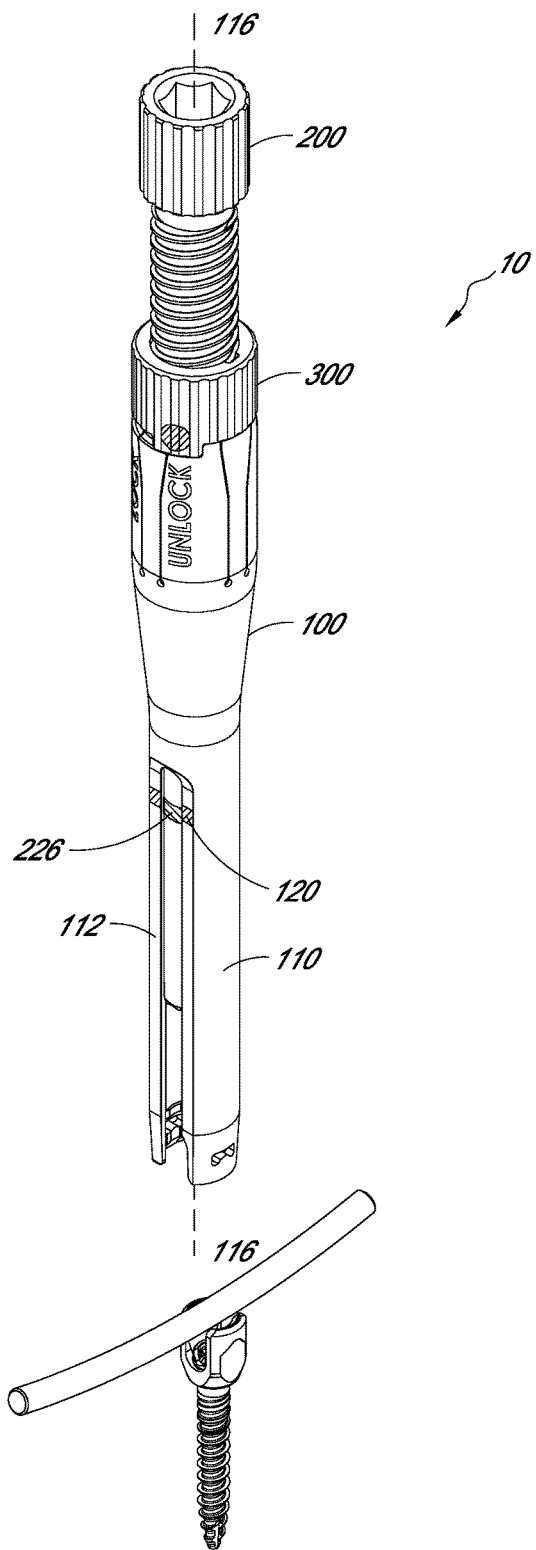
FIG. 14 is an embodiment of a method step of using the rod reducer of FIG. 1.

FIG. 14 shows the assembled rod reducer 10. The engagement member 200 can be inserted at least partially through the collar 300. The engagement member 200 can be inserted at least partially through the sleeve 100. In some methods of use, the rod reducer 10 is provided in the assembled state as shown in FIG. 14.

In other methods of use the rod reducer 10 is in a disassembled state. In the disassembled state, each component of the rod reducer 10 is uncoupled as shown in FIGS. 1-12. To assemble the rod reducer 10, one or more of the following steps can be performed.

Referring to FIGS. 2 and 14, the collar 300 can engage the cut out portion 130 of the sleeve 100. The collar 300 is free to rotate within the cut out portion 130 between an engaged position and a disengaged position as described herein. In some embodiments, the collar 300 and the cut out portion 130 have stop features at the engaged position and/or the disengaged position to help maintain the collar 300 in position. For example, the collar 300 can have detents and the cut out portion 130 can have a ball such that the ball engages the detents in the engaged position and the disengaged position. Any of a plurality of different types of stop features can be used. The stop feature can advantageously provide a tactile signal to the user to indicate when the engaged or disengaged position is reached. The shaft 222 of the engagement member 200 can be inserted into the collar 300.

Referring to FIGS. 4 and 9, the shaft 222 of the engagement member 200 can be inserted into the lumen 152 of the sleeve 100. The lumen 152 can have various shapes along the length of the sleeve. For instance, near the proximal end 104, the lumen 152 is formed from the threads 146, 150. The shaft 222 of the engagement member 200 can pass through the threads 146, 150. The shaft 222 of the engagement member 200 can couple with the mating portion 154 having engagement geometry. The engagement geometry can be any cross-sectional shape that ensures a mating configuration between the sleeve 100 and the engagement member 200. The mating portion 154 can include undercuts 156 which guide the engagement member 200 relative to the sleeve 100. The shaft 222 can include ridges 224 which interact with the undercuts 156 of the sleeve 100. The ridges 224 guide the engagement member 200 relative to the sleeve 100.

Referring to FIGS. 7 and 11, one or more components of the rod reducer 10 can include an alignment feature to aid in the alignment of the engagement member 200 and the sleeve 100. The first alignment feature 234 of the junction 232 of the engagement member 200 can be aligned with a second alignment feature 312 of the collar 300. In the illustrated embodiment, the pegs of the junction 232 can be aligned with the slots of the collar 300.

In some embodiments, the alignment of the first alignment feature 234 of the junction 232 with the second alignment feature 312 of the collar 300 allows the engagement member 200 to be inserted through the collar 300 and into the sleeve 100. In some embodiments, the collar 300 can be rotated to the engaged position to align the first alignment features 234 of the junction 232 and the collar 300. In the illustrated embodiment, the position of the first alignment feature 234 on the perimeter of the junction 232 is correlated with the position of the second alignment feature 312 on the inner perimeter of the collar 300 such that the first alignment feature 234 of the junction 232 can pass through the second alignment feature 312 of the collar 300 when the collar 300 is in the engaged position on the sleeve 100. In the engaged position, the tabs 132 are pushed inward, as described herein. The tabs 132 prevent the junction 232 from passing through the sleeve 100.

In some methods of use, the collar 300 can be rotated after the first alignment feature 234 of the junction 232 pass through the second alignment feature 312 of the collar 300. In some methods of use, the collar 300 can be rotated to the disengaged position after the first alignment feature 234 of the junction 232 pass through the second alignment feature 312 of the collar 300. The marking 310 can be aligned with the marking 126 of the sleeve 100. In the disengaged position, the second engagement feature 314 of the collar 300 does not engage the first engagement feature 144 of the tabs 132. In the disengaged position, the collar 300 does not push the tabs 132 inward.

The collar 300 can be in the disengaged position as shown in FIG. 14. In the disengaged position, the engagement member 200 can move longitudinally without engaging the threaded member 242 of the engagement member 200 with the threads 150 of the tabs 132. In the disengaged position, the tabs 132 do not engage the threaded member 242 of the engagement member 200. In the disengaged position, the engagement member 200 can be pushed to move distally within the sleeve 100. In the disengaged position, the engagement member 200 can be pulled to move proximally within the sleeve 100.

In some methods of use, the engagement member 200 is translated within the sleeve 100 until the first marking 226 of the engagement member 200 aligns with the marking 120 of the sleeve 100. FIG. 14 shows the alignment of the markings 120, 226. The first marking 226 can indicate the maximum distal position of the engagement member 200 within the sleeve 100 in order to couple the reducer 10 to the head 26 of the fastener 16. For instance, if the engagement member 200 is moved too far distally such that the first marking 226 is distal to the marking 120, then the shaft 222 may be too far in the lumen 152 and prevent the legs 110, 112 from deflecting sufficiently to couple around the head 26.

FIG. 14 shows each leg 110, 112 of the sleeve 100 which can be relatively straight when the engagement member 200 is inserted therein. Each leg 110, 112 can be parallel or substantially parallel to a longitudinal axis 116 of the sleeve 100 when the engagement member 200 is inserted therein. Each leg 110, 112 can have a neutral position in which the leg 110, 112 is equidistant from the longitudinal axis 116 from the proximal end of each leg 110, 112, to a distal end of each leg 110, 112. In some embodiments, the engagement member 200 does not pull the legs 110, 112 inward toward the longitudinal axis 116. In some embodiments, the engagement member 200 does not push the legs 110, 112 outward away from the longitudinal axis 116. In some embodiments, the engagement member 200 enforces the neutral position of the legs 110, 112.

In some embodiments, the rod reducer 10 is configured to be moved in a longitudinal direction toward the fastener 16. The longitudinal axis 116 of sleeve 100 can align with the longitudinal axis 36 of the head 26 of the fastener 16. The longitudinal axis 216 of engagement member 200 can align with the longitudinal axis 36 of the head 26 of the fastener 16.

In some methods of use, each leg 110, 112 can be deflected to accept the head 26 of the fastener 16. In some embodiments, the head 26 can interact with the first couplers 164 of each leg 110, 112 of the sleeve 100 to cause outward movement of the legs 110, 112. The first couplers 164 are shown in FIG. 6. In other embodiments, the head 26 can interact with another component of the sleeve 100 to cause outward movement of the legs 110, 112. The legs 110, 112 are deflected from a neutral position. The legs 110, 112 can be straight or substantially straight in the neutral position. In the illustrated embodiments, the legs 110, 112 are equidistant from the longitudinal axis 116 along a distal portion of the sleeve 100. The legs 110, 112 can be defected outward from the neutral position. When the legs 110, 112 are deflected, the distal end 102 of the sleeve is a greater distance from the longitudinal axis 116 than a proximal portion of the legs 110, 112.

The sleeve 100 can be moved longitudinally until first couplers 164 of each leg 110, 112 of the sleeve 100 engage the corresponding second couplers 44 of each side 40, 42 of the head 26 of the fastener 16. The fastener 16 is shown in FIG. 13. The legs 110, 112 can resume the neutral position when they are fully seated onto the head 26 of the fastener 16. As noted herein, the legs 110, 112 can be straight or substantially straight in the neutral position.

Figure 15:
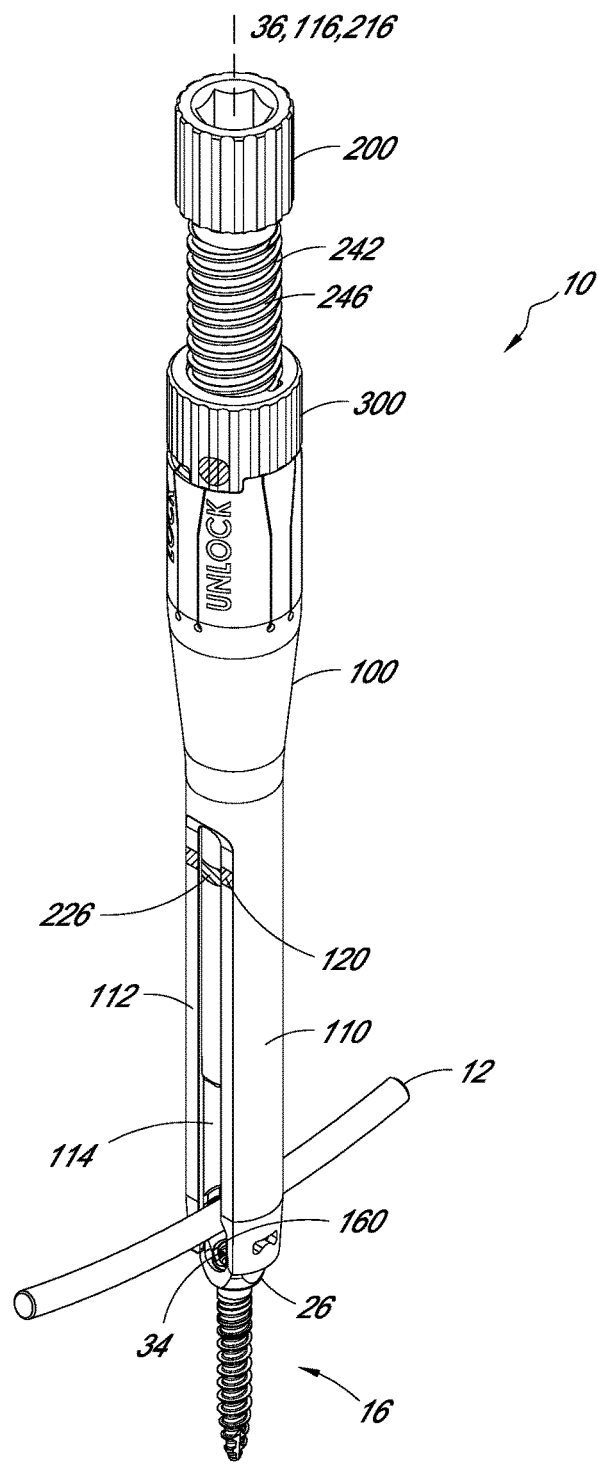
FIG. 15 is an embodiment of a method step of using the rod reducer of FIG. 1.

FIG. 15 shows the rod reducer 10 coupled with the fastener 16. In the illustrated embodiments, the first couplers 164 of each leg 110, 112 of the sleeve 100 engage the corresponding second couplers 44 of each side 40, 42 of the head 26 of the fastener 16. The channel 34 of the head 26 of the fastener 16 aligns with the slot 114 between the legs 110, 112 of the sleeve 100. The rod 12 can be located within the slot 114. The rod 12 can be located within the channel 34. Each notch 160, 162 can extend beyond the head 26 of the fastener 16. Each notch 160, 162 can extend more proximal than the proximal end 24 of the head 26 of the fastener 16.

Figure 16:
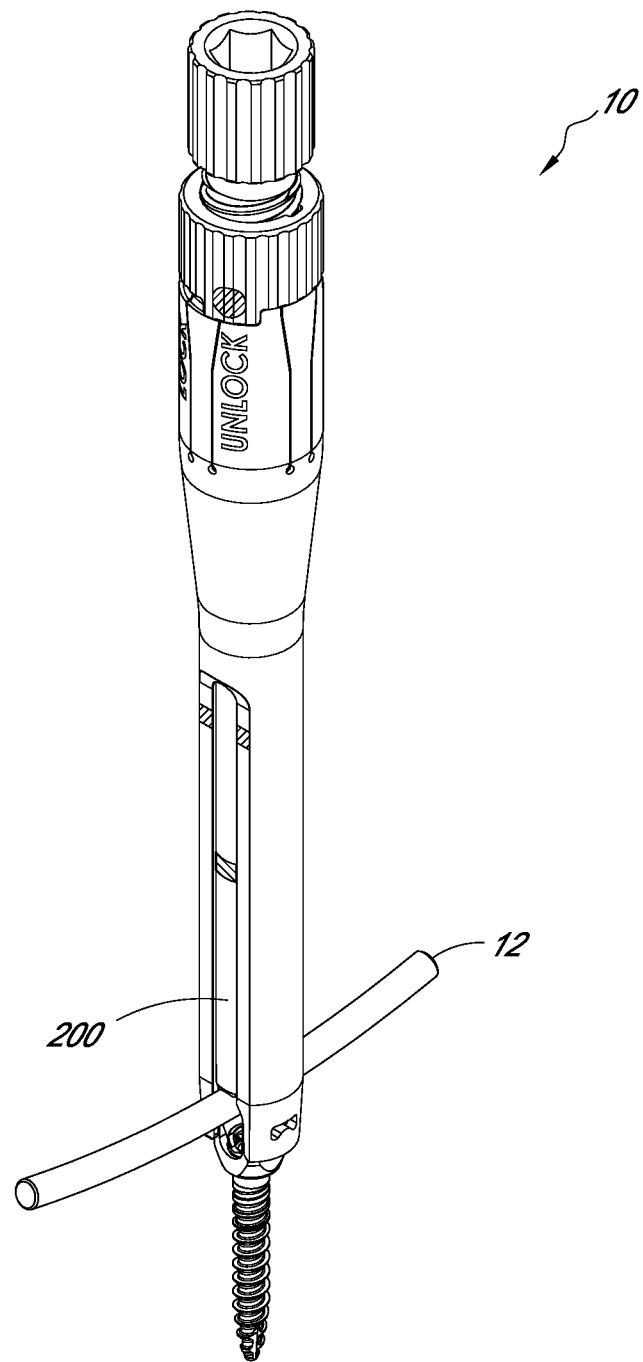
FIG. 16 is an embodiment of a method step of using the rod reducer of FIG. 1.

In some methods of use, the engagement member 200 is pushed within the sleeve 100. The engagement member 200 can be pushed into contact with the rod 12. FIG. 16 shows the engagement member 200 being pushed into contact with the rod. In some embodiments, the engagement member 200 can be pushed within the sleeve 100 until a third marking is aligned with the marking 120 on the sleeve 100. The third marking can be between the first marking 226 and the second marking 228. The third marking can indicate when the engagement member 200 is sufficiently coupled with the sleeve 100 in order to provide enough holding force to prevent the legs 110, 112 from deflecting and unintentionally disengaging from the head 26 of the fastener 16 as the rod 12 is reduced.

Figure 17:
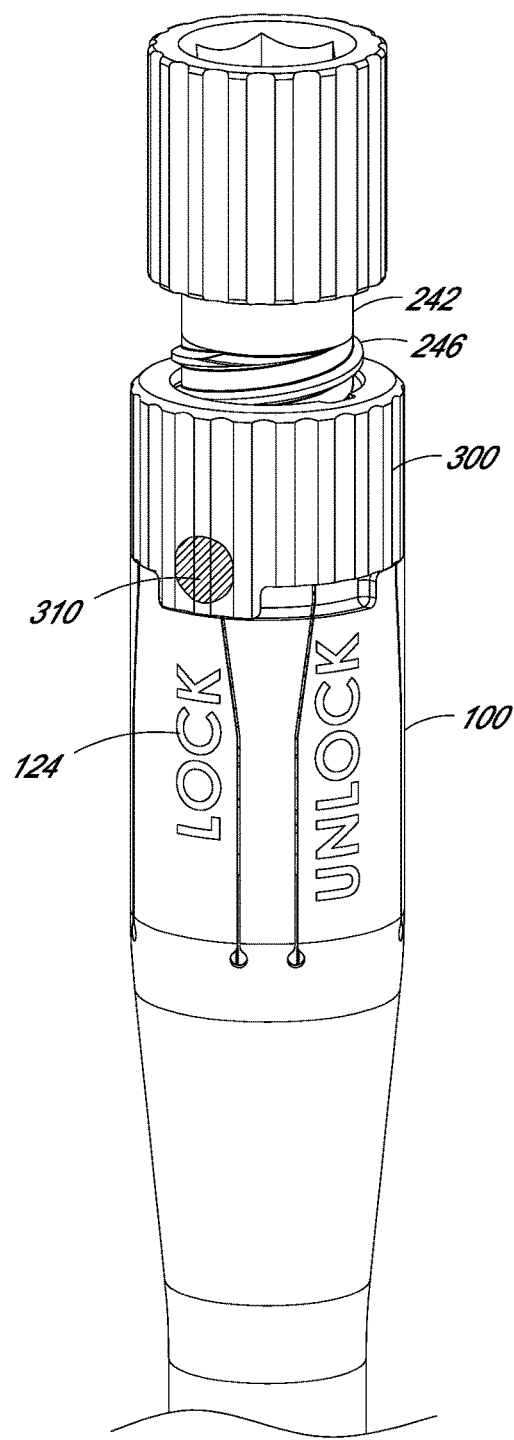
FIG. 17 is an embodiment of a method step of using the rod reducer of FIG. 1.

Referring back to FIG. 15, in some embodiments, the alignment of the first marking 226 of the engagement member 200 with the marking 120 of the sleeve 100 indicates alignment of the threads 150 of the tabs 132 with the threads 246 of the threaded member 242. In some embodiments, the alignment of the third marking of the engagement member 200 with the marking 120 of the sleeve 100 indicates alignment of the threads 150 of the tabs 132 with the threads 246 of the threaded member 242. The collar 300 can be rotated to the engaged position, as shown in FIG. 17. The marking 310 is aligned with the marking 124 of the sleeve 100. In the engaged position, the second engagement feature 314 of the collar 300 can engage the first engagement feature 144 of the tabs 132. In the engaged position, the collar 300 can push the tabs 132 inward. The tabs 132 when pushed inward form a smaller diameter than the threads 146 of the sleeve 100. The tabs 132 when pushed inward form a diameter which is the same or substantially similar to the diameter of the threaded member 242 of the engagement member 200.

In the engaged position, the threads 150 of the tabs 132 can interlock with the threads 246 of the threaded member 242. The threads 150 of the tabs 132 can engage the threaded member 242 and the rotation of the threaded member 242 can cause linear translation of the engagement member 200 within the sleeve 100. In the engaged position, the tabs 132 can engage the threaded member 242 of the engagement member 200. In some embodiments, in the engaged position, the engagement member 200 cannot be pushed within the sleeve 100. In some embodiments, in the engaged position, the engagement member 200 cannot be pulled within the sleeve 100. In the engaged position, the engagement member 200 can linearly translate when the threaded member 242 is rotated.

In some embodiments, in the engaged position the threads 150 of the tabs 132 can form a ratchet structure. The ratchet structure can allow the engagement member 200 to move longitudinally in a particular direction relative to the sleeve 100 and still allow the threaded member 242 of the engagement member 200 to engage with the threads 150 of the tabs 132. For example, the ratchet structure can allow the engagement member 200 to be pushed distally within the sleeve 100, but engages the engagement member 200 when pulled proximally within the sleeve 100. The engagement member 200 can be pushed to a position adjacent the rod 12 and the handle 206 can be rotated, which rotates the threaded member 242 to engage the threads 150 and drive the engagement member 200 distally.

Figure 18:
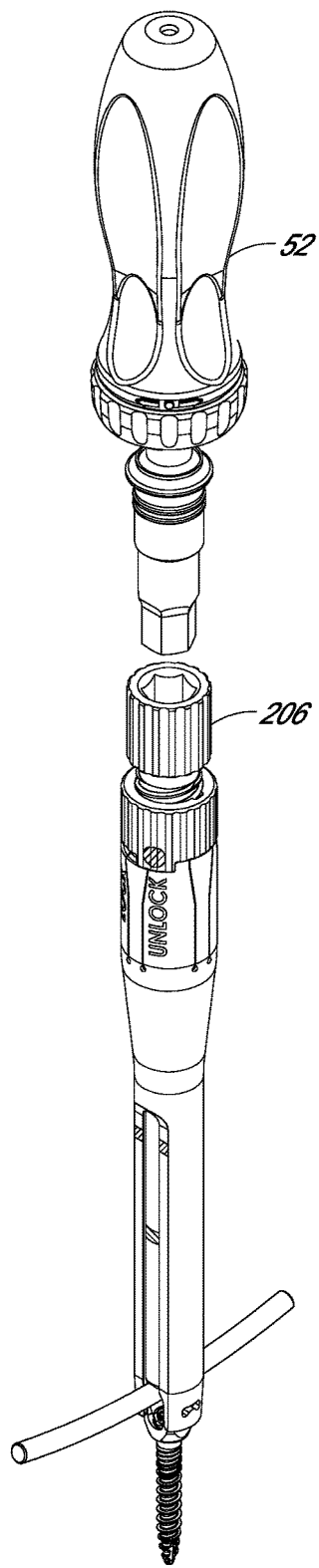
FIG. 18 is an embodiment of a method step of using the rod reducer of FIG. 1.
Figure 19:
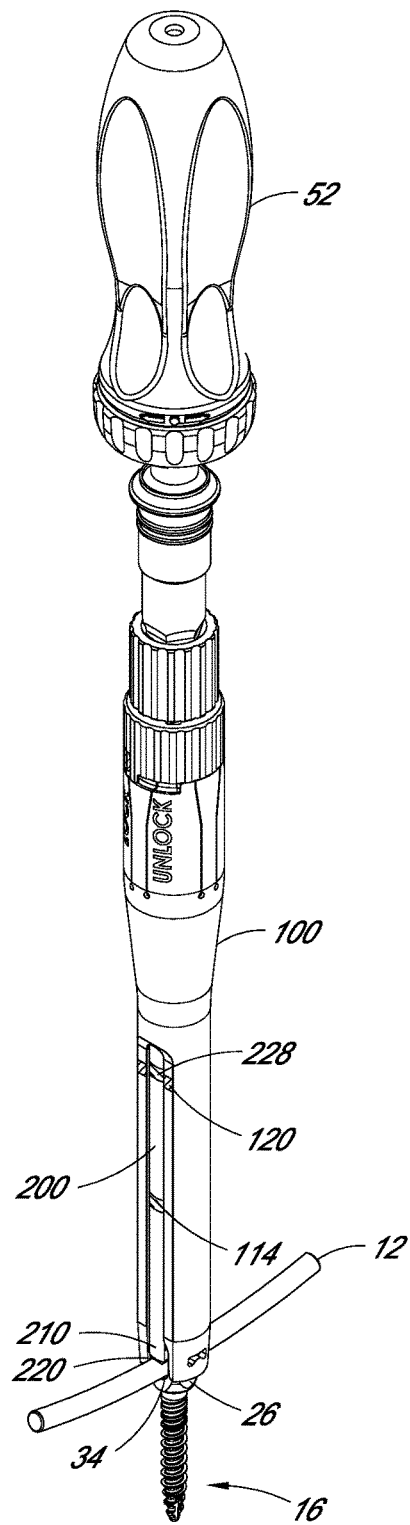
FIG. 19 is an embodiment of a method step of using the rod reducer of FIG. 1.

FIG. 18 shows a driver 52. The driver 52 can facilitate motion of the engagement member 200. In some methods of use, the driver 52 is utilized after the engagement member 200 makes contact with the rod 12. In other methods of use, the driver 52 is utilized before the engagement member 200 makes contact with the rod 12. The driver 52 can be utilized anytime the collar 300 is in the disengaged position to push or pull the engagement member 200 as shown in FIG. 18. The driver 52 can be utilized anytime the collar 300 is in the engaged position to rotate the engagement member 200 as shown in FIG. 19. In some methods of use, the driver 52 is not utilized. The handle 206 can be rotated to rotate the threaded member 242.

FIG. 19 shows the contact of the engagement member 200 with the rod 12. The distal end 202 of the engagement member 200 can include flange 210, 212. Each flange 210, 212 can have a distal end 220 to engage the rod 12. Each flange 210, 212 can have the same or similar dimension as the slot 114 of the sleeve 100. Each flange 210, 212 can have the same or similar dimension as the channel 34 of the head 26. In some embodiments, each flange 210, 212 can extend external to the head 26 of the fastener 16. In some embodiments, each flange 210, 212 can extend partially or completely within the head 26 of the fastener 16. The flanges 210, 212 can be points of contact between the engagement member 200 and the rod 12.

The threaded member 242 is rotated until the rod 12 is pushed distally within the channel 34 of the head 26 of the fastener. In some methods of use, the rod 12 is pushed into contact with the screw 20. In some methods of use, the rod 12 is pushed into contact with an intermediate object and the intermediate objected is pushed into contact with the screw 20.

In some methods of use, the engagement member 200 is translated within the sleeve 100 until the second marking 228 of the engagement member 200 aligns with the marking 120 of the sleeve 100. FIG. 19 shows the alignment of the markings 120, 228.

In some embodiments, the alignment of the second marking 228 of the engagement member 200 with the marking 120 of the sleeve 100 indicates that the rod 12 is lowered into the channel 34 of the head 26. The alignment of the markings 120, 228 can indicate that the rod 12 has been fully reduced.

Figure 20:
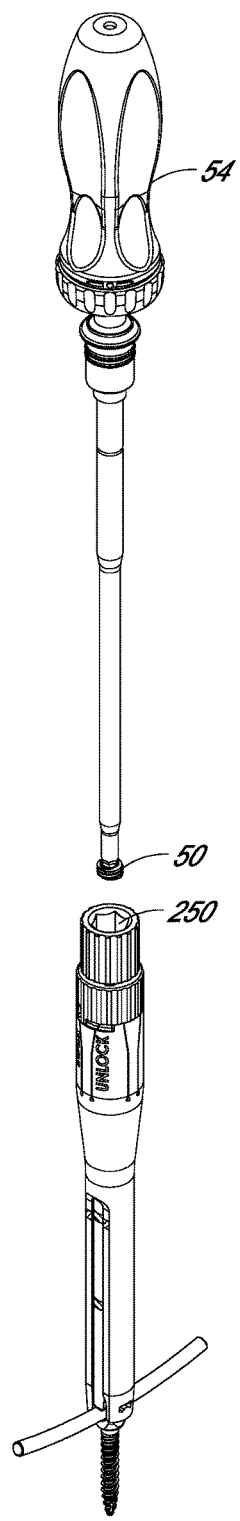
FIG. 20 is an embodiment of a method step of using the rod reducer of FIG. 1.
Figure 21:
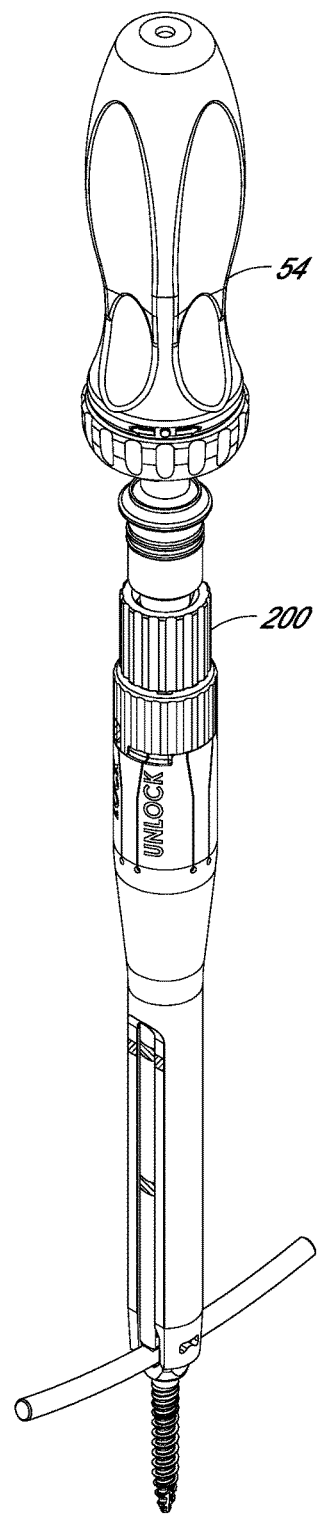
FIG. 21 is an embodiment of a method step of using the rod reducer of FIG. 1.

FIG. 20 shows a driver 54. The driver 54 can be coupled to the closure device 50. The driver 54 and the closure device 50 can be inserted within the lumen 250 of the engagement member 200 as shown in FIG. 21. The closure device 50 can engage the threads of the opening 46 of the head 26 of the fastener 16. The closure device 50 can secure the rod 12 to the fastener 16.

Referring back to FIG. 15, the rod reducer 10 can be removed from the fastener 16 after the rod 12 is secured. In some methods of use, the engagement member 200 is rotated to translate the shaft 222 proximally within the sleeve 100. The collar 300 can be in the engaged position. In some methods of use, the collar 300 is rotated to the disengaged position. The engagement member 200 can be pulled to translate the shaft 222 proximally within the sleeve 200. In some embodiments, the distal end 202 of the engagement member 200 is retracted beyond the legs 110, 112 prior to disengagement of the sleeve 100 from the fastener 16. In some embodiments, the distal end 202 of the engagement member 200 is retracted about to a midpoint of the legs 110, 112 prior to disengagement of the sleeve 100 from the fastener 16. The engagement member 200 can be retracted proximally until at least the first marking 226 is aligned with or proximal of the marking 120 of the sleeve 100 prior to disengagement of the sleeve 100 from the fastener 16. In some embodiments, the retraction of the engagement member 200 allows the legs 110, 112 to be deflected by the fastener 16, as described herein.

The sleeve 100 can be rotated to remove the rod reducer 10 from the fastener 16. The sleeve 100 can be rotated about the longitudinal axis 116 of the sleeve 100. The head 26 of the fastener 16 can deflect the legs 110, 112 outward. The rotation of the sleeve 100 relative to the fastener 16 can disengage the first couplers 164 of the sleeve from the second couplers 44 of the fastener 16. The external surface of the head 26 of the fastener 16 can interact with the first couplers 164 of the sleeve 100 to defect the legs 110, 112 outward. The notches 160, 162 can be sized to permit the sleeve 100 to be rotated past a leading edge of the head 26 of the fastener. The notches 160, 162 help facilitate uncoupling of the fastener 16 and the sleeve 100.

In some embodiments, the engagement member 200 can be translated proximally until the first alignment feature 234 of the junction 232 abuts the collar 300 in the disengaged position. The collar 300 can be rotated to the engaged position. The first alignment feature 234 of the junction 232 can align with the second alignment feature 312 of the collar 300 in the engaged position. In some embodiments, the collar is configured so that the first alignment feature 234 is aligned with the second alignment feature 312 when the collar is in the disengaged position, so that the engagement member 200 can be removed from the sleeve 100 without obstruction or without repositioning the collar. The engagement member 200 can be removed from the sleeve 100. The collar 300 can be removed from the sleeve 100. In some embodiments, the threaded member 242 can be removed from the junction 232.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A rod reducer comprising:
   a sleeve comprising a lumen and one or more tabs;
   an engagement member comprising a distal portion and a proximal portion, wherein the proximal portion is configured to be rotated relative to the distal portion;
   a collar coupled to the sleeve, wherein the collar is configured to deflect the tabs inward into the lumen,
   wherein the rod reducer has a first configuration wherein the tabs engage the proximal portion and the proximal portion can be rotated to translate the engagement member,
   wherein the rod reducer has a second configuration wherein the proximal portion can be pushed or pulled to translate the engagement member.

2. The rod reducer as in claim 1, wherein the sleeve comprises a pair of legs separated by a slot.

3. The rod reducer as in claim 2, wherein the pair of legs is configured to remain straight in the first configuration and the second configuration.

4. The rod reducer as in claim 1, wherein the collar is configured to be rotated about a longitudinal axis of the sleeve to switch between the first configuration and the second configuration.

5. The rod reducer as in claim 1, wherein the sleeve and the engagement member each comprise a marking, wherein alignment of the markings indicate a position to switch between the first configuration and the second configuration.

6. The rod reducer as in claim 1, wherein the sleeve and the engagement member each comprise a marking, wherein alignment of the markings indicates a distal position of the engagement member.

7. The rod reducer as in claim 1, wherein the sleeve and the engagement member each comprise a marking, wherein alignment of the markings indicate a maximum distal position of the engagement member for coupling the rod reducer to a fastener.

8. The rod reducer as in claim 1, wherein the tabs comprise threads and the proximal portion of the engagement member comprise threads.

9. The rod reducer as in claim 1, wherein the sleeve comprises one or more notches near a distal end, the one or more notches configured to allow the sleeve to rotate relative to a fastener.

10. The rod reducer as in claim 1, wherein the sleeve and the distal portion of the engagement member comprise a mating configuration.

11. The rod reducer as in claim 10, wherein the mating configuration comprises an undercut.

12. The rod reducer as in claim 10, wherein the rod reducer includes one or more alignment features configured to ensure alignment of the mating configuration.

13. The rod reducer as in claim 10, wherein in the mating configuration, the distal portion of the engagement member prevents a pair of legs of the sleeve from deflecting.

14. The rod reducer as in claim 1, wherein the engagement member comprises a lumen configured to accept a set screw.

15. A method of using a rod reducer comprising:
   pushing or pulling a proximal portion of an engagement member to translate a distal portion of the engagement member within a lumen of a sleeve, the sleeve comprising one or more tabs;
   rotating a collar to deflect one or more tabs of the sleeve into engagement with the proximal portion of the engagement member; and
   rotating the proximal portion of the engagement member to translate the distal portion of the engagement member within the lumen of the sleeve.

16. The method as in claim 15, further comprising engaging a thread of one or more tabs with a thread of the proximal portion of the engagement member.

17. The method as in claim 15, further comprising rotating the proximal portion of the engagement member relative to the distal portion of the engagement member.

18. The method as in claim 15, further comprising engaging an undercut of the sleeve with the distal portion of the engagement member.

19. The method as in claim 15, further comprising coupling a distal portion of the sleeve to a fastener.

20. The method as in claim 19, further comprising rotating the sleeve to decouple the distal portion of the sleeve from the fastener.

21. The method as in claim 15, further comprising aligning a marking of the sleeve with a marking of the engagement member prior to rotating the collar.

22. The method as in claim 21, wherein aligning the marking of the sleeve with the marking of the engagement member indicates that a thread of the one or more tabs aligns with a thread of the proximal portion of the engagement member.

23. The method as in claim 15, wherein the proximal portion of the engagement member is rotated until a marking of the sleeve is aligned with a marking of the engagement member indicating that the distal portion of the engagement member is in a distalmost position.

24. The method as in claim 21, wherein aligning the marking of the sleeve with the marking of the engagement member indicates when the distal portion of the engagement member is sufficiently coupled with the sleeve to prevent a pair of legs of the sleeve from unintentionally disengaging from a fastener.

* * * * *